(12) United States Patent
Groux et al.

(10) Patent No.: US 7,977,093 B2
(45) Date of Patent: Jul. 12, 2011

(54) OBTENTION OF FOOD- OR AUTO-ANTIGEN SPECIFIC TR1 CELLS FROM A LEUKOCYTE OR PBMC POPULATION

(75) Inventors: Hervé Groux, Le Rouret (FR); Françoise Cottrez, Le Rouret (FR); Arnaud Foussat, Biot (FR); Valerie Brun, Biot (FR)

(73) Assignees: INSERM (Institut National de la Sante et de la Recherche Medicale), Paris (FR), part interest; TXCELL, Valbonne (FR), part interest ( * ) Notice: Subject to any disclaimer, the term of this patent is extended or adjusted under 35 U.S.C. 154(b) by 126 days.

(21) Appl. No.: 11/994,337

(22) PCT Filed: Jul. 3, 2006

(86) PCT No.: PCT/IB2006/002801
§ 371 (c)(1),
(2), (4) Date: Feb. 26, 2008

(87) PCT Pub. No.: WO2007/010406
PCT Pub. Date: Jan. 25, 2007

(65) Prior Publication Data
US 2009/0075372 A1    Mar. 19, 2009

(30) Foreign Application Priority Data
Jul. 1, 2005  (EP) .................................. 05291429

(51) Int. Cl.
*C12N 5/0786* (2010.01)
*C12N 5/071* (2010.01)
*C12N 5/078* (2010.01)
*C12N 5/0783* (2010.01)

(52) U.S. Cl. ......................................... 435/326; 435/395
(58) Field of Classification Search ........................ None
See application file for complete search history.

(56) References Cited

U.S. PATENT DOCUMENTS
2004/0191235 A1 *   9/2004   Groux et al. ............... 424/93.71

FOREIGN PATENT DOCUMENTS
WO    WO 02/092793 A1 *  11/2002

OTHER PUBLICATIONS

Groux et al, Nature 389 (6652), 737 (1997)).*
Levings et al, J. Immunol. 166 (9), 5530 (2001).*
Doverskog, et al., "Physiology of cultured animal cells", Journal of Biotechnology 59 (1997), pp. 103-115.
Echalier, "*Drosophila* Cells in Culture", Textbook, Copyright 1997 by Academic Press, pp. 1-27.
Zheng, et al., "Generation Ex Vivo of TGF-{beta}-Producing Regulatory T Cells from CD4+CD25- Precursors", The Journal of Immunology, 2002; 169, pp. 4183-4189.

* cited by examiner

*Primary Examiner* — James Martinell
(74) *Attorney, Agent, or Firm* — Young & Thompson

(57) ABSTRACT

An in vitro method for the obtention of a food- or auto-antigen specific Tr1 cell population from a leukocyte or a PBMC population, includes stimulating the PBMC or leukocyte population with the food- or auto-antigen, and recovering the food- or auto-antigen specific Tr1 cell population from the stimulated cell population. Preferably, the PBMC or leukocyte population is re-stimulated at least once with the same antigen after step (1), in the presence of IL-2 and at least one interleukin selected from the group consisting of IL-4 and IL-13. The in vitro method may further include a third step of expanding the recovered antigen-specific Tr1 cell population, advantageously by contacting them with feeder cells capable of expressing factors necessary for the expansion. Preferably, the feeder cells are recombinant insect feeder cells.

39 Claims, 11 Drawing Sheets

Figure 1:
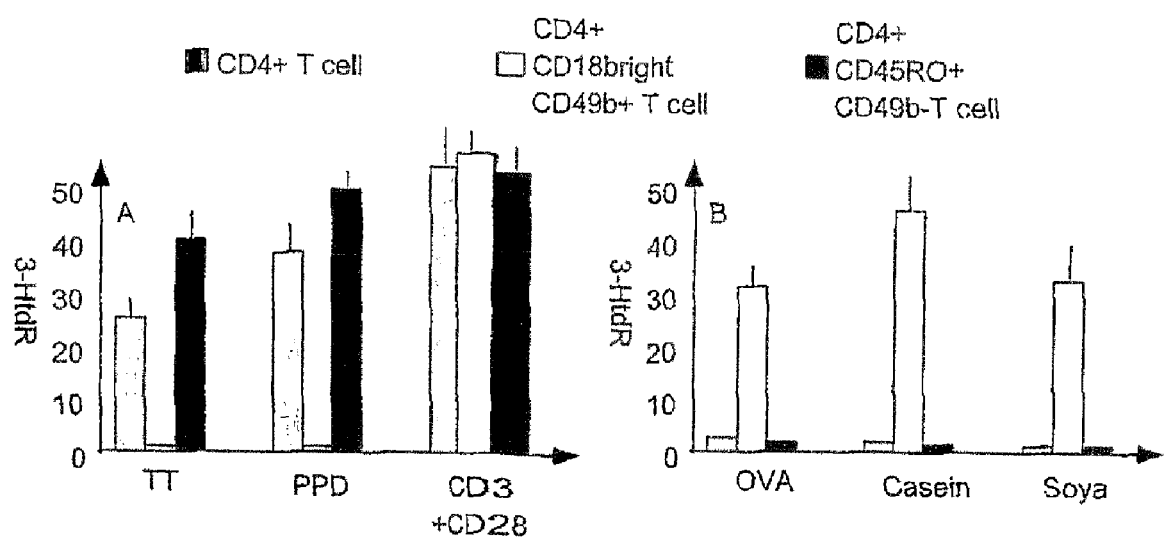

SEQUENCE LISTING

<160> NUMBER OF SEQ ID NOS: 26

<210> SEQ ID NO 1
<211> LENGTH: 708
<212> TYPE: DNA
<213> ORGANISM: Homo sapiens

<400> SEQUENCE: 1

| | | | | | | |
|---|---|---|---|---|---|---|
| atggattttc | aagtgcagat | tttcagcttc | ctgctaatca | gtgcctcagt | cataatatcc | 60 |
| agaggacaaa | ttgttctcac | ccagtctcca | gcaatcatgt | ctgcatctcc | aggggagaag | 120 |
| gtcaccatga | cctgcagtgc | cagctcaagt | gtaagttaca | tgaactggta | ccagcagaag | 180 |
| tcaggcacct | cccccaaaag | atggatttat | gacacatcca | aactggcttc | tggagtccct | 240 |
| gctcacttca | ggggcagtgg | gtctgggacc | tcttactctc | tcacaatcag | cggcatggag | 300 |
| gctgaagatg | ctgccactta | ttactgccag | cagtggagta | gtaacccatt | cacgttcggc | 360 |
| tcggggacaa | agttggaaat | aaaccgggct | gatactgcac | caactgtatc | catcttccca | 420 |
| ccatccagtg | agcagttaac | atctggaggt | gcctcagtcg | tgtgcttctt | gaacaacttc | 480 |
| taccccaaag | acatcaatgt | caagtggaag | attgatggca | gtgaacgaca | aaatggcgtc | 540 |
| ctgaacagtt | ggactgatca | ggacagcaaa | gacagcacct | acagcatgag | cagcacccctc | 600 |
| acgttgacca | aggacgagta | tgaacgacat | aacagctata | cctgtgaggc | cactcacaag | 660 |
| acatcaactt | cacccattgt | caagagcttc | aacaggaatg | agtgttag | | 708 |

<210> SEQ ID NO 2
<211> LENGTH: 1560
<212> TYPE: DNA
<213> ORGANISM: Homo sapiens

<400> SEQUENCE: 2

| | | | | | | |
|---|---|---|---|---|---|---|
| atggaaaggc | actggatctt | tctactcctg | ttgtcagtaa | ctgcaggtgt | ccactcccag | 60 |
| gtccagctgc | agcagtctgg | ggctgaactg | gcaagacctg | gggcctcagt | gaagatgtcc | 120 |
| tgcaaggctt | ctggctacac | ctttactagg | tacacgatgc | actgggtaaa | acagaggcct | 180 |
| ggacagggtc | tggaatggat | tggatacatt | aatcctagcc | gtggttatac | taattacaat | 240 |
| cagaagttca | aggacaaggc | cacattgact | acagacaaat | cctccagcac | agcctacatg | 300 |
| caactgagca | gcctgacatc | tgaggactct | gcagtctatt | actgtgcaag | atattatgat | 360 |
| gatcattact | gccttgacta | ctggggccaa | ggcaccactc | tcacagtctc | ctcagccaaa | 420 |
| acaacagccc | catcggtcta | tccactggcc | cctgtgtgtg | gagatacaac | tggctcctcg | 480 |
| gtgactctag | gatgcctggt | caagggttat | ttccctgagc | cagtgacctt | gacctggaac | 540 |
| tctggatccc | tgtccagtgg | tgtgcacacc | ttcccagctg | tcctgcagtc | tgacctctac | 600 |
| accctcagca | gctcagtgac | tgtaacctcg | agcacctggc | ccagccagtc | catcacctgc | 660 |
| aatgtggccc | acccggcaag | cagcaccaag | gtggacaaga | aaattgagcc | cagagggccc | 720 |
| acaatcaagc | cctgtcctcc | atgcaaatgc | ccagcaccta | acctcttggg | tggaccatcc | 780 |
| gtcttcatct | tccctccaaa | gatcaaggat | gtactcatga | tctccctgag | ccccatagtc | 840 |
| acatgtgtgg | tggtggatgt | gagcgaggat | gacccagatg | tccagatcag | ctggtttgtg | 900 |
| aacaacgtgg | aagtacacac | agctcagaca | caaacccata | gagaggatta | caacagtact | 960 |
| ctccgggtgg | tcagtgccct | ccccatccag | caccaggact | ggatgagtgg | caaggagttc | 1020 |
| aaatgcaagg | tcaacaacaa | agacctccca | gcgcccatcg | agagaaccat | ctcaaaaccc | 1080 |

-continued

| | |
|---|---|
| aaagggtcag taagagctcc acaggtatat gtcttgcctc caccagaaga agagatgact | 1140 |
| aagaaacagg tcactctgac ctgcatggtc acagacttca tgcctgaaga catttacgtg | 1200 |
| gagtggacca acaacgggaa aacagagcta aactacaaga acactgaacc agtcctggac | 1260 |
| tctgatggtt cttacttcat gtacagcaag ctgagagtgg aaaagaagaa ctgggtggaa | 1320 |
| agaaatagct actcctgttc agtggtccac gagggtctgc acaatcacca cacgactaag | 1380 |
| agcttctccc ggactccggg taaagaattc gctgtgggcc aggacacgca ggaggtcatc | 1440 |
| gtggtgccac actccttgcc ctttaaggtg gtggtgatct cagccatcct ggccctggtg | 1500 |
| gtgctcacca tcatctccct tatcatcctc atcatgcttt ggcagaagaa gccacgttag | 1560 |

<210> SEQ ID NO 3
<211> LENGTH: 867
<212> TYPE: DNA
<213> ORGANISM: Homo sapiens

<400> SEQUENCE: 3

| | |
|---|---|
| atgggccaca cacggaggca gggaacatca ccatccaagt gtccatacct caatttcttt | 60 |
| cagctcttgg tgctggctgg tctttctcac ttctgttcag gtgttatcca cgtgaccaag | 120 |
| gaagtgaaag aagtggcaac gctgtcctgt ggtcacaatg tttctgttga agagctggca | 180 |
| caaactcgca tctactggca aaaggagaag aaaatggtgc tgactatgat gtctggggac | 240 |
| atgaatatat ggcccgagta caagaaccgg accatctttg atatcactaa taacctctcc | 300 |
| attgtgatcc tggctctgcg cccatctgac gagggcacat acgagtgtgt tgttctgaag | 360 |
| tatgaaaaag acgctttcaa gcgggaacac ctggctgaag tgacgttatc agtcaaagct | 420 |
| gacttcccta cacctagtat atctgacttt gaaattccaa cttctaatat tagaaggata | 480 |
| atttgctcaa cctctggagg ttttccagag cctcacctct cctggttgga aaatggagaa | 540 |
| gaattaaatg ccatcaacac aacagtttcc caagatcctg aaactgagct ctatgctgtt | 600 |
| agcagcaaac tggattccaa tatgacaacc aaccacagct tcatgtgtct catcaagtat | 660 |
| ggacatttaa gagtgaatca gaccttcaac tggaatacaa ccaagcaaga gcattttcct | 720 |
| gataacctgc tcccatcctg gccattacc ttaatctcag taaatggaat ttttgtgata | 780 |
| tgctgcctga cctactgctt tgccccaaga tgcagagaga aaggaggaa tgagagattg | 840 |
| agaagggaaa gtgtacgccc tgtataa | 867 |

<210> SEQ ID NO 4
<211> LENGTH: 990
<212> TYPE: DNA
<213> ORGANISM: Homo sapiens

<400> SEQUENCE: 4

| | |
|---|---|
| atggatcccc agtgcactat gggactgagt aacattctct ttgtgatggc cttcctgctc | 60 |
| tctggtgctg ctcctctgaa gattcaagct tatttcaatg agactgcaga cctgccatgc | 120 |
| caatttgcaa actctcaaaa ccaaagcctg agtgagctag tagtattttg gcaggaccag | 180 |
| gaaaacttgg ttctgaatga ggtatactta ggcaaagaga aatttgacag tgttcattcc | 240 |
| aagtatatgg gccgcacaag ttttgattcg gacagttgga cctgagact tcacaatctt | 300 |
| cagatcaagg acaagggctt gtatcaatgt atcatccatc acaaaaagcc cacaggaatg | 360 |
| attcgcatcc accagatgaa ttctgaactg tcagtgcttg ctaacttcag tcaacctgaa | 420 |
| atagtaccaa tttctaatat aacagaaaat gtgtacataa atttgacctg ctcatctata | 480 |
| cacggttacc cagaacctaa gaagatgagt gttttgctaa gaaccaagaa ttcaactatc | 540 |

```
gagtatgatg gtattatgca gaaatctcaa gataatgtca cagaactgta cgacgtttcc    600
atcagcttgt ctgtttcatt ccctgatgtt acgagcaata tgaccatctt ctgtattctg    660
gaaactgaca agacgcggct tttatcttca cctttctcta tagagcttga ggaccctcag    720
cctcccccag accacattcc ttggattaca gctgtacttc aacagttat tatatgtgtg    780 atggttttct gtctaattct atggaaatgg aagaagaaga agcggcctcg caactcttat    840
aaatgtggaa ccaacacaat ggagagggaa gagagtgaac agaccaagaa aagagaaaaa    900
atccatatac ctgaaagatc tgatgaagcc cagcgtgttt ttaaaagttc gaagacatct    960
tcatgcgaca aaagtgatac atgttttttaa                                    990
```

```
<210> SEQ ID NO 5
<211> LENGTH: 462
<212> TYPE: DNA
<213> ORGANISM: Homo sapiens

<400> SEQUENCE: 5
atgtacagga tgcaactcct gtcttgcatt gcactaagtc ttgcacttgt cacaaacagt     60
gcacctactt caagttctac aaagaaaaca cagctacaac tggagcattt actgctggat    120
ttacagatga ttttgaatgg aattaataat tacaagaatc ccaaactcac caggatgctc    180
acatttaagt tttacatgcc caagaaggcc acagaactga acatcttca gtgtctagaa     240 gaagaactca aacctctgga ggaagtgcta aatttagctc aaagcaaaaa ctttcactta    300
agacccaggg acttaatcag caatatcaac gtaatagttc tggaactaaa gggatctgaa    360
acaacattca tgtgtgaata tgctgatgag acagcaacca ttgtagaatt ctgaacaga    420 tggattacct tttgtcaaag catcatctca acactgactt ga                      462
```

```
<210> SEQ ID NO 6
<211> LENGTH: 753
<212> TYPE: DNA
<213> ORGANISM: Homo sapiens

<400> SEQUENCE: 6
atggttgctg ggagcgacgc ggggcgggcc ctggggtcc tcagcgtggt ctgcctgctg      60
cactgctttg gtttcatcag ctgttttttcc caacaaatat atggtgttgt gtatgggaat    120
gtaactttcc atgtaccaag caatgtgcct ttaaaagagg tcctatggaa aaaacaaaag    180
gataaagttg cagaactgga aaattctgaa ttcagagctt tctcatcttt taaaaatagg    240
gtttatttag acactgtgtc aggtagcctc actatctaca acttaacatc atcagatgaa    300
gatgagtatg aaatggaatc gccaaatatt actgatacca tgaagttctt tctttatgtg    360
cttgagtctc ttccatctcc cacactaact tgtgcattga ctaatggaag cattgaagtc    420
caatgcatga taccagagca ttacaacagc catcgaggac ttataatgta ctcatgggat    480
tgtcctatgg agcaatgtaa acgtaactca accagtatat ttttaagat ggaaaatgat     540 cttccacaaa aaatacagtg tactcttagc aatccattat taatacaac atcatcaatc    600 attttgacaa cctgtatccc aagcagcggt cattcaagac acagatatgc acttatacc     660 ataccattag cagtaattac aacatgtatt gtgctgtata tgaatggtat tctgaaatgt    720
gacagaaaac cagacagaac caactccaat tga                                 753
```

```
<210> SEQ ID NO 7
<211> LENGTH: 462
<212> TYPE: DNA
<213> ORGANISM: Homo sapiens
```

```
<400> SEQUENCE: 7
atgggtctca cctcccaact gcttccccct ctgttcttcc tgctagcatg tgccggcaac    60
tttgtccacg gacacaagtg cgatatcacc ttacaggaga tcatcaaaac tttgaacagc   120
ctcacagagc agaagactct gtgcaccgag ttgaccgtaa cagacatctt tgctgcctcc   180
aagaacacaa ctgagaagga aaccttctgc agggctgcga ctgtgctccg gcagttctac   240
agccaccatg agaaggacac tcgctgcctg ggtgcgactg cacagcagtt ccacaggcac   300
aagcagctga tccgattcct gaaacggctc gacaggaacc tctggggcct ggcgggcttg   360
aattcctgtc ctgtgaagga agccaaccag agtacgttgg aaaacttctt ggaaaggcta   420
aagacgatca tgagagagaa atattcaaag tgttcgagct ga                      462

<210> SEQ ID NO 8
<211> LENGTH: 441
<212> TYPE: DNA
<213> ORGANISM: Homo sapiens

<400> SEQUENCE: 8
atgcatccgc tcctcaatcc tctcctgttg gcactgggcc tcatggcgct tttgttgacc    60
acggtcattg ctctcacttg ccttggcggc tttgcctccc caggccctgt gcctccctct   120
acagccctca gggagctcat tgaggagctg gtcaacatca cccagaacca gaaggctccg   180
ctctgcaatg gcagcatggt atggagcatc aacctgacag ctggcatgta ctgtgcagcc   240
ctggaatccc tgatcaacgt gtcaggctgc agtgccatcg agaagaccca gaggatgctg   300
agcggattct gcccgcacaa ggtctcagct gggcagtttt ccagcttgca tgtccgagac   360
accaaaatcg aggtggccca gtttgtaaag gacctgctct acatttaaa gaaactttt   420 cgcgagggac agttcaactg a                                            441

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atgcggatcc atggattttc aagtgcag                                      28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgcgaattc ctaacactca ttcctgttg                                     29

<210> SEQ ID NO 11
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgcccgcgg ggtacccact gaaaactctg actcaac                            37
```

```
<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
actggacagg gatccagagt tc                                              22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gaactctgga tccctgtcca gtg                                             23

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atgcgaattc tttacccgga gtccgggaga agctc                                35

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgcgaattc gctgtgggcc aggacacgca g                                    31

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atgcgggccc aagcttctaa cgtggcttct tctgccaaag                           40

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atgcggatcc atgtacagga tgcaactcct                                      30
```

-continued

```
<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atgcgaattc tcaagtcagt gttgagatga                                           30

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgctggatc catggttgct gggagcgacg c                                         31

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgctaagct ttcaattgga gttggttctg t                                         31

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgcggatcc atgggtctca cctcccaact                                           30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
atgcaagctt tcagctcgaa cactttgaat                                           30

<210> SEQ ID NO 23
<211> LENGTH: 386
<212> TYPE: PRT
<213> ORGANISM: Gallus sp.

<400> SEQUENCE: 23

Met Gly Ser Ile Gly Ala Ala Ser Met Glu Phe Cys Phe Asp Val Phe
  1               5                  10                  15

Lys Glu Leu Lys Val His His Ala Asn Glu Asn Ile Phe Tyr Cys Pro
             20                  25                  30

Ile Ala Ile Met Ser Ala Leu Ala Met Val Tyr Leu Gly Ala Lys Asp
         35                  40                  45
```

```
Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
        115                 120                 125

Gly Leu Glu Pro Ile Asn Phe Gln Thr Ala Ala Asp Gln Ala Arg Glu
    130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Ala Phe Lys Asp Glu
            180                 185                 190

Asp Thr Gln Ala Met Pro Phe Arg Val Thr Glu Gln Glu Ser Lys Pro
        195                 200                 205

Val Gln Met Met Tyr Gln Ile Gly Leu Phe Arg Val Ala Ser Met Ala
    210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
        275                 280                 285

Glu Glu Lys Tyr Asn Leu Thr Ser Val Leu Met Ala Met Gly Ile Thr
    290                 295                 300

Asp Val Phe Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
        355                 360                 365

Ile Lys His Ile Ala Thr Asn Ala Val Leu Phe Phe Gly Arg Cys Val
    370                 375                 380

Ser Pro
385

<210> SEQ ID NO 24
<211> LENGTH: 214
<212> TYPE: PRT
<213> ORGANISM: Bos taurus

<400> SEQUENCE: 24

Met Lys Leu Leu Ile Leu Thr Cys Leu Val Ala Val Ala Leu Ala Arg
1               5                   10                  15

Pro Lys His Pro Ile Lys His Gln Gly Leu Pro Gln Glu Val Leu Asn
            20                  25                  30
```

-continued

```
Glu Asn Leu Leu Arg Phe Phe Val Ala Pro Phe Pro Glu Val Phe Gly
             35                  40                  45

Lys Glu Lys Val Asn Glu Leu Ser Lys Asp Ile Gly Ser Glu Ser Thr
 50                  55                  60

Glu Asp Gln Ala Met Glu Asp Ile Lys Gln Met Glu Ala Glu Ser Ile
 65                  70                  75                  80

Ser Ser Ser Glu Glu Ile Val Pro Asn Ser Val Glu Gln Lys His Ile
                 85                  90                  95

Gln Lys Glu Asp Val Pro Ser Glu Arg Tyr Leu Gly Tyr Leu Glu Gln
            100                 105                 110

Leu Leu Arg Leu Lys Lys Tyr Lys Val Pro Gln Leu Glu Ile Val Pro
            115                 120                 125

Asn Ser Ala Glu Glu Arg Leu His Ser Met Lys Glu Gly Ile His Ala
        130                 135                 140

Gln Gln Lys Glu Pro Met Ile Gly Val Asn Gln Glu Leu Ala Tyr Phe
145                 150                 155                 160

Tyr Pro Glu Leu Phe Arg Gln Phe Tyr Gln Leu Asp Ala Tyr Pro Ser
                165                 170                 175

Gly Ala Trp Tyr Tyr Val Pro Leu Gly Thr Gln Tyr Thr Asp Ala Pro
            180                 185                 190

Ser Phe Ser Asp Ile Pro Asn Pro Ile Gly Ser Glu Asn Ser Glu Lys
        195                 200                 205

Thr Thr Met Pro Leu Trp
    210

<210> SEQ ID NO 25
<211> LENGTH: 224
<212> TYPE: PRT
<213> ORGANISM: Bos taurus

<400> SEQUENCE: 25

Met Lys Val Leu Ile Leu Ala Cys Leu Val Ala Leu Ala Leu Ala Arg
 1               5                  10                  15

Glu Leu Glu Glu Leu Asn Val Pro Gly Glu Ile Val Glu Ser Leu Ser
             20                  25                  30

Ser Ser Glu Glu Ser Ile Thr Arg Ile Asn Lys Lys Ile Glu Lys Phe
         35                  40                  45

Gln Ser Glu Glu Gln Gln Gln Thr Glu Asp Glu Leu Gln Asp Lys Ile
     50                  55                  60

His Pro Phe Ala Gln Thr Gln Ser Leu Val Tyr Pro Phe Pro Gly Pro
 65                  70                  75                  80

Ile His Asn Ser Leu Pro Gln Asn Ile Pro Pro Leu Thr Gln Thr Pro
                 85                  90                  95

Val Val Val Pro Pro Phe Leu Gln Pro Glu Val Met Gly Val Ser Lys
            100                 105                 110

Val Lys Glu Ala Met Ala Pro Lys His Lys Glu Met Pro Phe Pro Lys
        115                 120                 125

Tyr Pro Val Glu Pro Phe Thr Glu Ser Gln Ser Leu Thr Leu Thr Asp
    130                 135                 140

Val Glu Asn Leu His Leu Pro Leu Pro Leu Leu Gln Ser Trp Met His
145                 150                 155                 160

Gln Pro His Gln Pro Leu Pro Pro Thr Val Met Phe Pro Pro Gln Ser
                165                 170                 175

Val Leu Ser Leu Ser Gln Ser Lys Val Leu Pro Val Pro Gln Lys Ala
            180                 185                 190
```

```
Val Pro Tyr Pro Gln Arg Asp Met Pro Ile Gln Ala Phe Leu Leu Tyr
        195                 200                 205

Gln Glu Pro Val Leu Gly Pro Val Arg Gly Pro Phe Pro Ile Ile Val
    210                 215                 220

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Asp Glu Ala Asp
1
```

OBTENTION OF FOOD- OR AUTO-ANTIGEN SPECIFIC TR1 CELLS FROM A LEUKOCYTE OR PBMC POPULATION

The invention relates to an in vitro method for the obtention of a food- or auto-antigen specific Tr1 cell population from a leukocyte or a PBMC population, which comprises stimulating the PBMC or leukocyte population with the food- or auto-antigen, and recovering the food- or auto-antigen specific Tr1 cell population from the stimulated cell population. Preferably, the PBMC or leukocyte population is re-stimulated at least once with the same antigen after step (1), in the presence of IL-2 and at least one interleukin selected from the group consisting of IL-4 and IL-13. The in vitro method may further comprise a third step of expanding the recovered antigen-specific Tr1 cell population, advantageously by contacting them with feeder cells capable of expressing factors necessary for said expansion. Preferably, the feeder cells are recombinant insect feeder cells.

Among the T cell populations, there is now accumulating evidence for a novel functionally distinct subpopulation of T cells, called Tr1 regulatory cells or Tr1 cells. The inventors showed that T regulatory 1 (Tr1) cells could be used to treat inflammatory diseases (i.e. Crohn's disease (H. Groux et al. Nature 1997, 389, 737-742), skin inflammation (Foussat et al. 2003 J. Immunol. 171, 5018-5026), atherosclerosis (Mallat et al. Circulation 2003, 108, 1232-1237) or multiple sclerosis (Barrat et al. 2002, 195, 603-616). In all these models it was shown that anti-inflammatory Tr1 cells were directed against a specific antigen and that the delivery of that antigen, preferentially on the site of inflammation, was required to stimulate Tr1 cells to induce their anti-inflammatory functions. Therefore, in order to use Tr1 cells to treat human diseases one has to be able to isolate antigen-specific Tr1 cells. However this has proven to be very difficult.

The inventors have also shown that Tr1 cells express specific surface markers and could be characterized by the coexpression of the CD3 and CD4 markers as well as CD49b expression and a high expression level of CD18, and, where appropriate, by the demonstration of an over-expression of genes encoding the proteins CD4, PSGL-1, PECAM-1 and alphaV/beta3 (see the international patent application published with the number WO 2005/000344).

Surprisingly the inventors have observed that purified Tr1 cells isolated from human blood based on the expression of these markers (and consequently Tr1 cells present in a PBMC or leukocyte population) proliferated vigorously in response to food- or auto-antigens and that the proliferative response of these cells could be maintained by the stimulation using both IL-2 and IL-4 (IL for interleukin). This potential offers an important advantage over the prior art, since according to the common knowledge of the skilled person, it was previously necessary to firstly isolate antigen-specific naïve T cells from a PBMC population, secondly to induce the differentiation of antigen-specific Tr1 cells, whereas it is now possible to obtain food- or auto-antigen specific Tr1 cells directly from a PBMC (or leukocyte) population. In the present invention, the in vitro method to obtain food- or auto-antigen specific Tr1 cells is simplificated, and safety for the patients to whom these cells are administered is increased, since these cells have not changed in terms of quality.

Consequently, the subject matter of the present invention is an in vitro method for the obtention of a food- or auto-antigen specific Tr1 cell population from a leukocyte population or a peripheral blood mononuclear cell (PBMC) population, said method comprising:

1) stimulating the PBMC or leukocyte population with the food- or auto-antigen,
2) recovering the food- or auto-antigen specific Tr1 cell population from the stimulated cell population.

Leukocytes encompass several types of cells which are characterized by their importance, their distribution, their number, their lifetime and their potentiality. These types are the following: the polynuclear or granular leukocytes, among which one finds the eosinophilic, the neutrophilic and the basophilic leukocytes, and the mononuclear cells, or peripheral blood mononuclear cells (PBMCs), which are large white blood cells and consist in the cell types of the immune system (lymphocytes and monocytes). The leukocytes or the PBMCs can be separated from the peripheral blood by any method known to those skilled in the art. Advantageously, for the separation of the PBMCs, centrifugation may be used, preferably density gradient centrifugation, preferably discontinuous density gradient centrifugation. An alternative is the use of specific monoclonal antibodies. In certain embodiments PBMC are typically isolated from the whole blood product by means of Ficoll-Hypaque, using standard procedures. In other embodiments the PBMCs are recovered by means of leukapheresis.

The term "antigen" in the expression "antigen-specific Tr1 cell population" refers to an immunogenic peptide. Immunogenic peptides are peptides that can bind to major histocompatibility complex (MHC) molecules of an individual and that are recognized by the T cell receptors of said individual.

The terms protein, polypeptide, peptide employed in the present application refer indifferently to a molecule formed by the union in a long chain of smaller elements, the amino acids.

The term "food-antigen" refers to an immunogenic peptide which comes from foodstuffs, such as food antigens of the following non-limiting list: bovine antigens such as lipocalin, Ca-binding S100, alpha-lactalbumin, beta-lactoglobulin, bovine serum albumin, immunoglobulin or caseins. Food-antigens may also be atlantic salmon antigens such as parvalbumin, chicken antigens such as ovomucoid, ovalbumin, Ag22, conalbumin, lysozyme or chicken serum albumin, shrimp antigens such as tropomyosin, wheat antigens such as agglutinin or omega-5 gliadin, celery antigens such as celery profilin, carrot antigens such as carrot profilin, apple antigens such as thaumatin, apple lipid transfer protein, apple profilin, pear antigens such as pear profilin, isoflavone reductase, avocado antigens such as endochitinase, apricot antigens such as apricot lipid transfer protein, peach antigens such as peach lipid transfer protein or peach profilin, soybean antigens such as HPS, soybean profilin or (SAM22) PR-10 prot.

The term "auto-antigen" refers to an immunogenic peptide derived from a protein of said individual. It may be, by way of example, an auto-antigen of the following non-limiting list: acetylcholine receptor, actin, adenin nucleotide translocator, β-adrenoreceptor, aromatic L-amino acid decarboxylase, asioaloglycoprotein receptor, bactericidal/permeability increasing protein (BPi), calcium sensing receptor, cholesterol side chain cleavage enzyme, collagen type IV $\alpha_\gamma$-chain, cytochrome P450 2D6, desmin, desmoglein-1, desmoglein-3, F-actin, GM-gangliosides, glutamate decarboxylase, glutamate receptor, H/K ATPase, 17-α-hydroxylase, 21-hydroxylase, IA-2 (ICAS12), insulin, insulin receptor, intrinsic factor type 1, leucocyte function antigen 1, myelin associated glycoprotein, myelin basic protein, myelin oligodendrocyte protein, myosin, P80-coilin, pyruvate deshydrogenase complex E2 (PDC-E2), sodium iodide symporter, SOX-10, thyroid and eye muscle shared protein, thyroglobulin, thyroid peroxydase, thyrotropin receptor, tissue transglutaminase, transcription coactivator p75, tryptophan hydroxylase, tyrosinase, tyrosine hydroxylase, ACTH, aminoacyl-tRNA-hystidyl synthetase, cardiolipin, carbonic anhydrase II, cebtromere associated proteins, DNA-dependant nucleosome-stimulated ATPase, fibrillarin, fibronectin, glucose 6 phosphate isomerase, beta 2-glycoprotein I, golgin (95, 97, 160, 180), heat shock proteins, hemidesmosomal protein 180, histone H2A, H2B, keratin, IgE receptor, Ku-DNA protein kinase, Ku-nucleoprotein, La phosphoprotein, myeloperoxydase, proteinase 3, RNA polymerase I-III, signal recognition protein, topoisomerase I, tubulin, vimenscin, myelin associated oligodendrocyte basic protein (MOBP), proteolipid protein, oligodendrocyte specific protein (OSP/Claudin 11), cyclic nucleotide 3'phosphodiesterase (CNPase), BP antigen 1 (BPAG1-e), transaldolase (TAL), human mitochondrial autoantigens PDC-E2 (Novo 1 and 2), OGDC-E2 (Novo 3), and BCOADC-E2 (Novo 4), bullous pemphigoid (BP)180, laminin 5 (LN5), DEAD (SEQ ID NO: 26)-box protein 48 (DDX48) or insulinoma-associated antigen-2.

Antigens such as bacterial or virus antigens are excluded from the expression "food- or auto-antigen".

The food- or auto-antigen, which is mostly composed of a sequence of amino-acids, may be synthesized by the usual techniques, such as the Fmoc method, if the sequence of amino-acids is known, or by known recombinant DNA technologies (see Sambrook et al. (Molecular Cloning: A Laboratory Manual, 2nd Edition, Cold Spring Harbor Laboratory press (1989)). Some food- or auto-antigens are also commercially available (Sigma, L'Isle d'Abeau, France). The food- or auto-antigen may be also extracted.

Preferably, the food- or auto-antigen specific Tr1 cell population is obtained from a PBMC population.

More preferably, the PBMC or leukocyte population is re-stimulated at least once with the same antigen after step (1), in the presence of interleukin-2 (IL-2) and at least one interleukin selected from the group consisting of interleukin-4 (IL-4) and interleukin-13 (IL-13).

The frequency of food- or auto-antigen stimulation may be at least once, preferably once a week, over a few weeks (usually about three), or several times at intervals of five to twelve days. Multiple stimulations can be performed by exchanging a portion of the culture supernatant with the same amount of fresh PBMC or leukocyte culture medium containing the antigen.

The IL-2 and IL-4 used for re-stimulation of the PBMC or leukocyte population may be synthesized or recombinant interleukins, and the skilled person is with wide experience of methods to obtain such interleukins (see for example Sambrook et al. (Molecular Cloning: A Laboratory Manual, 2nd Edition, Cold Spring Harbor Laboratory press (1989)). IL-2 and IL-4 can be purchased from different sources, such as R&D Systems and Peprotech.

Preferably, the food- or auto-antigen is a recombinant or a synthesized antigen.

More preferably, the food-antigen is selected from the group comprising ovalbumin, casein, soya protein, fragments, variants and mixtures thereof.

The term "variant" of the food- or auto-antigen refers herein to an antigen that is almost identical to the natural antigen and which shares the same biological activity. The minimal difference between the natural antigen and its variant may lie for example in an amino-acid substitution, deletion, and/or addition. Such variants may contain for example conservative amino acid substitutions in which amino acid residues are replaced with amino acid residues having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta.-branched side chains (e.g., threonine, valine, isoleucine) and aromatic side chains (e.g., tyrosine, phenylalanine, tryptophan, histidine).

Most preferably, the food-antigen is selected from the group comprising chicken egg ovalbumin of sequence SEQ ID NO 23, bovin alpha Sl-casein of sequence SEQ ID NO 24, bovin beta-casein of sequence SEQ ID NO 25, and sequences having at least 70%, preferably 75, 77, 80, 82, 85, 87, 90, 92, 95, 96, 97, 98, 99% of identity with one of the sequences SEQ ID NO 23, SEQ ID NO 24 and SEQ ID NO 25.

In another preferred embodiment, the auto-antigen is selected from the group comprising insulin, myelin basic protein, fragments, variants and mixtures thereof.

The expression "stimulating the PBMC or leukocyte population with the food- or auto-antigen" as used herein means to add the antigen to the PBMC or leukocyte population and culture to react with T cells of said PBMC or leukocyte population. To produce a population of food- or auto-antigen specific Tr1 cells, the PBMC or leukocyte population is contacted with an antigen according to the present invention in a form suitable to trigger a primary activation signal in the T cells of said PBMC or leukocyte population, that is to say the antigen is presented to the PBMC or leukocyte population such that a signal is triggered in the T cells through the CD3/TCR complex. For example, the antigen can be presented to the PBMCs or leukocytes in a soluble form (either directly to form complexes with the MHC molecules expressed by the PBMCs or leukocytes or the antigen can be coupled either to a soluble, a polymeric or a surface (plastic, . . . ) bound form of MHC molecules) or by an antigen presenting cell (APC) in conduction with an MHC molecule. An antigen presenting cell (APC), such as a B cell, macrophage, monocyte, dendritic cell, Langerhans cell, or other cell which can present antigen to the T cells of said PBMC or leukocyte population, can be incubated with the PBMCs or leukocytes in the presence of the antigen (for example a soluble antigen) such that the antigen presenting cell presents the antigen to the PBMCs or leukocytes. Alternatively, the APCs can be preincubated with the antigen before being added to the PBMCs or leukocytes. Alternatively, a cell expressing the food- or auto-antigen can be incubated with the PBMC or leukocyte population.

Preferably, the stimulation of the PBMC or leukocyte population is performed in the wells of a microplate, a cell culture flask or a cell culture bag. The PBMC or leukocyte culture media which may be used are very well known by the skilled person: for example, the PBMCs or leukocytes may be stimulated in an RPMI medium supplemented with human serum or with X-vivo 15 (Cambrex).

Advantageously, the PBMC population stimulated at step (1) contains from $0.01 \times 10^6$ to $100 \times 10^6$ cells/mL, preferably from $0.2 \times 10^6$ to $5 \times 10^6$ cells/mL, more preferably from $0.1 \times 10^6$ to $3 \times 10^6$ cells/mL, even more preferably from $0.5 \times 10^6$ to $2.5 \times 10^6$ cells/mL, and most preferably from $1 \times 10^6$ to $2 \times 10^6$ cells/mL.

More advantageously, the food- or auto-antigen used for stimulation of the PBMC population at step (1) is in a soluble form from 0.1 µg/mL to 5 mg/mL preferably from 1 to 200 µg/mL.

It is however known from the man skilled in the art that the specific quantity of the food- or auto-antigen used for stimulation of the PBMC or leukocyte population depends on which food- or auto-antigen is used.

In another particular embodiment, the PBMC or leukocyte population is incubated, before stimulation at step (1), with a cell division fluorescent marker allowing to determine, by cytofluorometry, that when the fluorescence intensity of the stimulated cell population is at least twice lower than the fluorescence intensity of the PBMC or leukocyte population, that cell division has occurred in said stimulated cell population, and that said stimulated cell population which is recovered at step (2) is the antigen-specific Tr1 cell population.

Such a method, which allows to monitor cell division using fluorescent markers, is well known by the man skilled in the art and is very well appropriate for use at step (2) of recovering the antigen-specific Tr1 cell population, since the stimulated cell population whose fluorescence intensity is at least twice lower than the fluorescence intensity of the PBMC or leukocyte population, comprises the food or auto-antigen specific Tr1 cell population. Advantageously, the stimulated cell population whose fluorescence intensity is at least twice lower than the fluorescence intensity of the PBMC or leukocyte population, is the food or auto-antigen specific Tr1 cell population.

Preferably, the cell division fluorescent marker is the carboxyfluorescein diacetate succinimidyl ester (CFSE) marker, the oregon green 488 carboxylic acid diacetate (Carboxy-DFFDA SE) marker or the PKH26 (from the discoverer, Paul Karl Horan, PKH) marker, all being among others commercially available at Invitrogen.

The step (2) of recovering the food- or auto-antigen specific Tr1 cell population, can be performed by various methods well known by the skilled person. For example, Tr1 cells can be identified and/or purified by Elisa, flow cytometry, immunoaffinity chromatography with labelled antibodies directed against said Tr1 cell markers, for example with:
APC—conjugated anti-CD4 (RPA-T4)—Becton Dickinson (APC for allophycocyanine)
PC5—conjugated anti-CD3 (UCHT-1)—Caltag (PC5 for phycoerythrine-cyanine 5)
PE—conjugated anti-CD18 (6.7)—Becton Dickinson (PE for phycoerythrine)
FITC—conjugated anti-CD49b (AK-7)—Becton Dickinson or PE-labelled mouse anti-human CD49b (12F1-H6) (FITC for fluoresceine-isothiocyanate).

Specific Tr1 cell markers are now well known by the skilled person, and are sufficiently described in the international patent application WO 2005/000344.

Thus, in a preferred embodiment, the antigen-specific Tr1 cell population is recovered at step (2) by cytofluorometry using fluorescent labelled antibodies directed against proteins present at the surface of the cells of said antigen-specific Tr1 cell population.

ELISA tests and intracellular staining may also be used to measure IL-4, IL-10, and IFN-γ expression and to identify the Tr1 cells through their cytokine expression profile. Such methods are usually employed by the skilled person. For example, the supernatant obtained after step (1) of stimulation may be contacted with NIP-labelled antibodies directed against IL-4, IL-10 and IFN-γ expression (NIP for (4-hydroxy-5-iodo-3-nitrophenyl)acetyl (NIP), followed by peroxidase-labelled anti-NIP antibody and ABTS addition (ABTS for 2,2'-azino-di (3-ethyl-benzthiazoline-6-sulfonate) (from R&D Systems, Minneapolis, Minn., and Chiron Corp., Emmeryville, Calif.).

Preferably, the antigen-specific Tr1 cell population is recovered at step (2) by a cloning technique, such as advantageously by limiting dilution. Such methods are well known from the skilled person and will not be further disclosed in the present description.

It has to be envisaged that these methods of recovery of the antigen-specific Tr1 cell population may be employed alone or in combination. For example, the "CFSE method" may be used in combination with the cytofluorometry, or with the cloning limiting dilution technique. It is also possible to use the cytofluorometry followed by a cloning technique.

The PBMC or leukocyte population is preferably a mammal population. It may be a human as well as a non-human mammal (dog, cat, mice, rat, animals of agricultural interest such as livestock and fowl, etc. . . . ). More preferably, the PBMC or leukocyte population is a human population.

Advantageously, the invention further comprises:
3) expanding the antigen-specific Tr1 cell population recovered at step (2) in a culture medium Mp.

The culture medium Mp may be of any kind, provided that it is appropriate for said antigen-specific Tr1 cell population, and will be easily selected by the skilled person (Schneider's medium, serum free media, . . . ).

In the present application, the terms "expansion", "proliferation" and "growth" may be employed in an interchangeable way and refer to the increasing number of cells in a cell population. Preferably, the antigen-specific Tr1 cell population is expanded exponentially.

Advantageously, the step (3) of expanding the antigen-specific Tr1 cell population consists in contacting said cell population with CD3+CD28 beads (for example purchased from Dynal, Oslo, Norway) in the presence of IL-2 and IL-4.

In a particularly advantageous embodiment, the step (3) of expanding the antigen-specific Tr1 cell population requires the presence of a group of factors in the culture medium Mp, said expanding step comprising:
a) cultivating at a temperature $T_1$ in a culture medium Mf, feeder cells capable of expressing the factors of said group, such $T_1$ allowing the proliferation of said feeder cells,
b) contacting the feeder cells obtained at step (a) cleared or not of their culture medium Mf, with the antigen-specific Tr1 cell population contained in the culture medium Mp, wherein said culture medium Mp does not initially contain the group of factors, in order to obtain a mixture containing the antigen-specific Tr1 cell population, feeder cells and the culture medium Mp,
c) cultivating the mixture obtained at step (b) containing the factors of the group which are expressed by the feeder cells in the culture medium Mp, wherein said step (c) of cultivating is carried out at a temperature $T_2$ which is at least about 35° C., such that:
the antigen-specific Tr1 cell population proliferates, and
the feeder cells do not proliferate,
and wherein the antigen-specific Tr1 cell population is expanded,
d) recovering the antigen-specific Tr1 cell population so expanded.

The ratio [feeder cells:antigen-specific Tr1 cell population] is indifferent when adding the feeder cells to the antigen-specific Tr1 cell population (step (b)). Advantageously, this ratio may be [1:1].

Feeder cells may be of any type, provided that they do not proliferate at the culture temperature of the antigen-specific Tr1 cell population $T_2$, which is at least about 35° C.

The expression "at least about 35° C." means that the temperature may vary from 0.1° C. below 35° C. (from 34.9° C. to 35° C.). The skilled person is anyway aware of such minimal variations of temperature.

The skilled person who is with wide experience of cell culture, knows the specific conditions to be used, in particular the optimal culture temperatures $T_1$ and $T_2$ of each of feeder cell population and antigen-specific Tr1 cell population. The culture medium Mf may be of any kind, provided that it is appropriate for said feeder cell type, and will be easily selected by the skilled person (Schneider's medium, ... ).

It has to be considered that the step (b) of contacting the feeder cells with the antigen-specific Tr1 cell population, and the step (c) of cultivating the mixture at the temperature $T_2$, are usually simultaneous steps: before contacting, the feeder cells and the antigen-specific Tr1 cell population are cultivated separately, respectively one at the temperature $T_1$ in the culture medium Mf and the other at the temperature $T_2$ in the culture medium Mp. Then, the feeder cells "alone", or the culture medium Mf containing the feeder cells, is/are contacted with the antigen-specific Tr1 cell population which is present in its culture medium Mp and which is being cultivated at the temperature $T_2$. Consequently, the feeder cells pass immediately from the temperature $T_1$ to the temperature $T_2$ and stop to proliferate, unlike the antigen-specific Tr1 cell population, which is expanded thanks to the group of factors which are expressed by the feeder cells.

It is possible to maintain during a long time in vitro exponential growth of the antigen-specific Tr1 cell population, such as at least two or three months, by re-contacting feeder cells regularly, for example every week, with said antigen-specific Tr1 cell population.

More advantageously, the feeder cells die during step (c) because of the temperature $T_2$ which is no more appropriate for feeder cell culture. Most advantageously, the cell membrane fragments of the feeder cells that result from death of said cells are eliminated at step (d).

After a sufficient time of cultivating the antigen-specific Tr1 cell population at step (c) such as preferably several hours, the obtained culture medium Mp is composed of a mixture of the antigen-specific Tr1 cell population, viable feeder cells and optionally cell membrane fragments of the feeder cells, and the expanded antigen-specific Tr1 cell population has to be recovered at step (d). Such a recovery can be made by separating the antigen-specific Tr1 cell population from the viable feeder cells and optionally said cell membrane fragments using any appropriate separation method well known by the man skilled in the art, such as for example flow cytometry using a specific labelled ligand capable to bind at the surface of the feeder cells or a cell surface protein of the antigen-specific Tr1 cell population. Other methods may also be employed, such as washing methods and/or centrifugation such as density gradient centrifugation using separation media like Ficoll®, such a centrifugation being an appropriate method for eliminating cell membrane fragments.

It has to be noted that the elimination of the cell membrane fragments of the feeder cells is not compulsory but recommended, all the more when the expanded antigen-specific Tr1 cell population is intended to be administered to mammals. Otherwise, there is a risk that said expanded antigen-specific Tr1 cell population is contaminated.

Advantageously, the group of factors comprise factors anchored to the cell membrane of the feeder cells and factors secreted by said feeder cells. More advantageously, the factors of said group interact with cell surface proteins of the antigen-specific Tr1 cell population to be expanded.

When the feeder cells are cultivated at step (a), they express some factors of the group at their cell membrane surface and some other factors in the culture medium Mf. At the step (b) of contacting, the "membrane factors" are already anchored to the feeder cell membrane, but the "secreted factors" may be eliminated if the feeder cells are previously cleared of their culture medium Mf. Anyway, both of the "membrane factors" and the "secreted factors" are expressed by the feeder cells at step (c), even if the feeder cells no more proliferate, and until death of said feeder cells. It is even possible that the "membrane factors" anchored to the cell membrane fragments of the dead feeder cells still play a role in the production of the antigen-specific Tr1 cell population.

The antigen-specific Tr1 cell population which is expanded has cell surface proteins which are implicated in the cell signals allowing its expansion. Such cell surface proteins are activated thanks to specific ligands, or factors, which are provided in the present invention by the feeder cells: feeder cells express the group of factors allowing the expansion of the antigen-specific Tr1 cell population. The man skilled in the art knows which specific factors have to be expressed by the feeder cells such that these factors interact with a cell surface protein of the antigen-specific Tr1 cell population.

Even more preferably, the feeder cells are recombinant cells and contain heterologous nucleic acids encoding the factors of said group.

The expressions "recombinant cell" or "recombinant feeder cell" refer to the introduction in said cells of heterologous nucleic acids encoding the factors of the group. Such an introduction encompasses a variety of techniques useful for introduction of nucleic acids into feeder cells including electroporation, calcium-phosphate precipitation, DEAE-dextran treatment, lipofection, microinjection and infection with viral vectors. Such suitable methods are very well known by the skilled person, and can be found for example in Sambrook et al. (Molecular Cloning: A Laboratory Manual, 2nd Edition, Cold Spring Harbor Laboratory press (1989)). The nucleic acids to be introduced may be, for example, DNA encompassing the genes encoding the factors susceptible to interact with cell surface proteins of the antigen-specific Tr1 cell population to be expanded, genomic DNA fragments, sense strand RNA or recombinant expression vectors containing cDNA encoding such genes. The heterologous nucleic acids can encode the full length factors or alternatively it can encode peptidic fragments thereof that are sufficient to allow the production of the antigen-specific Tr1 cell population in accordance with the present invention, when introduced into the feeder cells. The nucleic acids can encode the natural ligands (co-stimulatory proteins) of the cell surface proteins of the antigen-specific Tr1 cell population, or fragments thereof, or modified forms of the ligands or fragments thereof. The invention is intended to include the use of fragments, mutants, or variants (e.g., modified forms) of the factors that retain the ability to enhance the expansion of the antigen-specific Tr1 cell population. A "variant" of a factor means a protein that shares a significant homology with the natural ligand and which is implicated in expansion of the antigen-specific Tr1 cell population. The terms biologically active or biologically active form of a protein include forms of factors that are capable of effecting expansion of the antigen-specific Tr1 cell population. One skilled in the art can select such factor variants based on their ability to enhance cell expansion upon introduction of nucleic acids encoding the factors in the feeder cells. The ability of a specific variant of factor to enhance expansion of an antigen-specific Tr1 cell population can be readily determined, for example, by comparing the recombinant feeder cells with non-recombinant feeder cells by any known assay or method. Furthermore, it will be appreciated by those skilled in the art that changes in the primary amino acid sequence of the factors are likely to be tolerated without significantly impairing the ability of the proteins to allow the expansion of the antigen-specific Tr1 cell population. Accordingly, variants of the factors that have amino acid substitutions, deletions and/or additions as compared to the naturally occurring amino acid sequences of comparable native factors, yet still retain the functional activity of the natural forms of the factors as described herein are also encompassed by the invention. Such variants may contain for example conservative amino acid substitutions (see supra).

The nucleic acids are in a form suitable for the factor expression, said form containing all of the coding and regulatory sequences required for transcription and translation of a gene, which may include a promoter, an enhancer and a polyadenylation signal, and optionally a sequence necessary for transport of the factor to the surface of the feeder cells, including an N-terminal signal sequence. Regulatory sequences can also be selected to provide constitutive or inducible transcription. The expression of the factor at the surface of the feeder cell can be confirmed by immunofluorescent staining of the cells. For example, cells may be stained with a fluorescently labeled monoclonal antibody reactive against the co-stimulatory molecule or with a fluorescently labeled soluble receptor which binds the factor. The skilled person, who knows very well the factors to be expressed by the feeder cells, also knows appropriate monoclonal antibodies which recognize factors expressed by the feeder cells. Alternatively, labelled soluble ligand proteins which bind to the factors can be used to detect their expression on the feeder cell surface. The techniques and devices employed for detecting immunofluorescent stained cells are very well known by the skilled person preferably, a fluorescence-activated cell sorter (FACS) is used for detection.

When the nucleic acid encoding a factor is operably linked to regulatory elements it is typically carried in a vector, including for example plasmids and viruses. Thus, a nucleic acid comprising a nucleotide sequence encoding a factor of the present invention operably linked to regulatory control elements, is also referred to herein as an "expression vector". Expression vectors will be chosen relative to the feeder cell type to be transformed. For example, when the feeder cells are *drosophila* insect feeder cells, *drosophila* constitutive vectors available for expression of proteins in cultured insect cells include the pAc series (Smith et al., (1983) Mol. Cell Biol. 3:2156-2165) and the pVL series (Lucklow, V. A., and Summers, M. D., (1989) Virology 170:31-39).

Moreover, it is preferred that the feeder cells do not have any intrinsic class I and/or II major histocompatibility complex (MHC) molecule at their surface. It means that these cells do not naturally express MHC molecules, unless they have been genetically transformed. The absence of these intrinsic class I and/or II MHC molecules at the surface of the feeder cells is crucial to avoid an allogeneic response between the feeder cells and the antigen-specific Tr1 cell population. As a result, the feeder cells of the present invention may be used to expand an antigen-specific Tr1 cell population from any donor in a short time period.

In a more particular embodiment, the feeder cells are cleared of their culture medium Mf at step (b).

Preferably, the feeder cells are insect feeder cells, with $T_1$ being inferior to $T_2$.

Any appropriate insect feeder cell may be used in the present invention, provided that it fulfills the above mentioned conditions. It may be for example insect feeder cells of the Sf9 (among others deposited at the ATCC with the number CRL 1711 or at the DSMZ with the number ACC 125, and marketed by BD Biosciences Pharmingen, US), Sf21 (among others deposited at the DSMZ with the number ACC 119, and also marketed by BD Biosciences Pharmingen, US) or the S2 cell line. Preferably, the insect feeder cells are from the S2 *drosophila* cell line. The S2 *drosophila* cell line is well known by the man skilled in the art, and has been widely disclosed in the prior art. The S2 *drosophila* cell line is commercially available (Invitrogen, France, etc. . . . ), and has been deposited in particular at the German collection of micro-organisms and culture cells DSMZ ("Deutsche Sammlung von Mikroorganismen und Zellkulturen") with the number ACC 130, and disclosed in Schneider, J Embryol Exp Morphol, 27:1972, 353; it has also been deposited at the American type culture collection ATCC with the number CRL 1963. Preferably, the insect feeder cells are from the S2 *drosophila* cell line deposited on Mar. 25, 2005 at the National Collection of Micro-organisms Cultures (CNCM, Pasteur Institute, Paris) under the number I-3407.

A great advantage provided by the use of insect feeder cells when a mammal cell population, and here an antigen-specific Tr1 cell population, is to be expanded, is that (1) feeder cells and mammal cells do not proliferate at the same temperature ($T_1$ is inferior to $T_2$ and $T_2$ is at least about 35° C.), and (2) mammal viruses do not proliferate in insect feeder cells, thus avoiding the possible virus contamination of the antigen-specific Tr1 cell population from the feeder cells.

Most preferably, the culture medium Mp is a serum-free culture medium. Media exempt from any biological contaminant, such as commercially available serum-free culture media (XVIVO-15 from BioWhittaker, Walkersville, Md.; AIM V medium from Invitrogen, etc. . . . ), are preferred.

Most preferably, the culture medium Mf is a serum-free culture medium. Media exempt from any biological contaminant, such as for example well known and commercially available serum-free culture media (Schneider's medium without serum marketed by BioWhittaker, Walkersville, Md. GIBCO® serum-free insect cell culture media such as SFM marketed by Invitrogen, or Insectagro® serum-free media marketed by Krackeler Scientific Inc., US, etc. . . . ), are preferred in order to avoid subsequent contamination of the cell population P.

More advantageously, the feeder cells are recombinant feeder cells expressing the group of recombinant factors which interact with the following cell surface proteins of the antigen-specific Tr1 cell population to be expanded:
the CD3/TCR protein complex,
the CD28 protein,
the CD2 protein,
the interleukin-2 (IL-2) receptor, and
the interleukin-4 (IL-4) receptor.

Indeed, for the expansion of the antigen-specific Tr1 cell population, stimulation of the TCR/CD3 complex (TCR for T cell receptor and CD for cell differentiation antigen) is required for delivery of a primary activation signal in a T cell. An anti-CD3 monoclonal antibody can be used to activate a population of T cells via the TCR/CD3 complex, advantageously a modified anti-CD3 antibody, wherein the modification of the anti-CD3 antibody consists in the replacement of the intracytoplasmic domain with a transmembrane domain, such that said modified anti-CD3 antibody anchors to the cellular membrane of the feeder cells and interacts with the CD3/TCR protein complex of the T cells.

Furthermore, a number of proteins on the surface of T cells, interchangeably termed "co-stimulatory molecules" or "co-stimulators," have been implicated in regulating the transition of a resting T cell to blast transformation, and subsequent proliferation and differentiation. Thus, in addition to the primary activation signal provided through the TCR/CD3 complex, induction of T cell responses requires a second co-stimulatory signal. One co-stimulatory or accessory molecule, CD28, is believed to initiate or regulate a signal transduction pathway that is distinct from those stimulated by the TCR complex.

The factor interacting with the CD28 protein present at the surface of the antigen-specific Tr1 cells and which is expressed by the feeder cells, may be an anti-CD28 monoclonal antibody or a fragment thereof capable of crosslinking the CD28 molecule; in such a case, modification of the anti-CD28 monoclonal antibody can be envisaged by adding a transmembrane domain in order that it anchors to the cell surface of the feeder cells. Preferably, the natural ligand for CD28 is employed instead of the anti-CD28 monoclonal antibody, that is to say for example a member of the B7 family of proteins, such as B7-1(CD80) and B7-2 (CD86) proteins.

Another co-stimulatory molecule, CD2, is implicated in the cell signals allowing expansion of the antigen-specific Tr1 cell population. Similarly, the factor expressed by the feeder cells which interacts with CD2 may be an anti-CD2 monoclonal antibody or a fragment thereof capable of crosslinking the CD2 molecule; modification of the anti-CD2 monoclonal antibody can be envisaged by adding a transmembrane domain for anchoring to the cell surface of the feeder cells. Preferably, the natural ligand for CD2 is employed instead of the anti-CD2 monoclonal antibody, that is to say the CD58 protein.

In addition to the factors which are anchored to the cell membrane of the feeder cells, factors which are secreted, such as interleukins, are also required for expansion of the antigen-specific Tr1 cell population. Among these interleukins are the IL-2, which interacts with the IL-2 receptor present at the surface of the antigen-specific Tr1 cells, and either the IL-4 or the IL-13, which interacts with the IL-4 receptor of the antigen-specific Tr1 cells.

Most advantageously, the group of recombinant factors comprise:
  the modified anti-CD3 antibody, wherein the modification of the anti-CD3 antibody consists in the replacement of the anti-CD3 intracytoplasmic domain of the anti-CD3 heavy chain with a transmembrane domain, said modified anti-CD3 antibody being anchored to the cell membrane of the feeder cells and being susceptible to interact with the CD3/TCR protein complex of the T cells, or a variant thereof,
  the CD80 or CD86 protein, preferably the CD80 protein, anchored to the cell membrane of the feeder cells, which is susceptible to interact with the CD28 protein of the T cells, or a variant thereof, and
  the CD58 protein anchored to the cell membrane of the feeder cells, which is susceptible to interact with the CD2 protein of the Tr1 cells, or a variant thereof,
  the IL-2 secreted by the feeder cells, which is susceptible to interact with the IL-2 receptor of the Tr1 cells, or a variant thereof, and
  an interleukin selected from the group comprising IL-4 and interleukin 13 (IL-13), preferably IL-4, said interleukin being secreted by the feeder cells and being susceptible to interact with the IL-4 receptor of the Tr1 cells, or a variant thereof.

Preferably, the transmembrane domain which replaces the intracytoplasmic domain of the anti-CD3 antibody heavy chain is the transmembrane domain of the platelet derived growth factor (PDGF).

Factors which are expressed by the feeder cells may be of any origin. Preferably, they are of the same origin than that of the PBMC or leukocyte population from which the antigen-specific Tr1 cell population is obtained. More advantageously, the PBMC or leukocyte population is a human population. Most preferably, the factors of said group are of human origin.

Preferably, the light chain of the modified anti-CD3 antibody is encoded by the heterologous nucleic acid of sequence SEQ ID NO 1 or any nucleic acid having at least 70% of identity with SEQ ID NO 1, and wherein the heavy chain of the modified anti-CD3 antibody is encoded by the heterologous nucleic acid of sequence SEQ ID NO 2, or any nucleic acid having at least 70% of identity with SEQ ID NO 2.

More preferably, the CD80 protein is encoded by the heterologous nucleic acid of sequence SEQ ID NO 3, or any nucleic acid having at least 70% of identity with SEQ ID NO 3.

Advantageously, the CD86 protein is encoded by the heterologous nucleic acid of sequence SEQ ID NO 4, or any nucleic acid having at least 70% of identity with SEQ ID NO 4.

Even more preferably, the CD58 protein is encoded by the heterologous nucleic acid of sequence SEQ ID NO 6, or any nucleic acid having at least 70% of identity with SEQ ID NO 6.

In a preferred embodiment, the IL-2 is encoded by the heterologous nucleic acid of sequence SEQ ID NO 5, or any nucleic acid having at least 70% of identity with SEQ ID NO 5.

Advantageously, the IL-4 is encoded by the heterologous nucleic acid of sequence SEQ ID NO 7 or any nucleic acid having at least 70% of identity with SEQ ID NO 7.

More advantageously, the IL-13 is encoded by the heterologous nucleic acid of sequence SEQ ID NO 8, or any nucleic acid having at least 70% of identity with SEQ ID NO 8.

The expression "nucleic acid molecule having at least 70% of identity with SEQ ID No. X" refers to any sequence which has at least 70, 75, 80, 85, 90, 95 or 99% of identity with said sequence SEQ ID No. X.

Generally, after several hours of culture of the antigen-specific Tr1 cell population to be expanded such as 12 hours, preferably after 24 hours of culture, more preferably 48 hours, there is not any more viable feeder cells in the culture medium Mp. Advantageously, the expanded antigen-specific Tr1 cell population is recovered when all the feeder cells are dead, which allows firstly to obtain a larger expanded antigen-specific Tr1 cell population, and secondly to recover rapidly and easily the antigen-specific Tr1 cell population by eliminating the cell membrane fragments of the feeder cells, for example by washing methods and/or density gradient centrifugation, as disclosed above.

Thus, in a preferred embodiment, the antigen-specific Tr1 cell population so expanded is recovered at step (d) after having cultivated the antigen-specific Tr1 cell population at step (c) during at least 12 hours, advantageously 24 hours.

By percentage of identity between two nucleic acids (or nucleic acid sequences) or two proteic sequences in the present invention, it is meant a percentage of identical nucleotides or amino-acids between the two sequences to compare, obtained after the best alignment; this percentage is purely statistical, and the differences between the two sequences are randomly distributed and all along their length. The best alignment or optimal alignment is the alignment corresponding to the highest percentage of identity between the two sequences to compare, which is calculated such as herein after. The sequence comparisons between two nucleic acids or two proteic sequences are usually performed by comparing these sequences after their optimal alignment, said comparison being performed for one segment or for one "comparison window", to identify and compare local regions of sequence similarity. The optimal alignment of sequences for the comparison can be performed manually or by means of the algorithm of local homology of Smith and Waterman (1981) (Ad. App. Math. 2:482), by means of the algorithm of local homology of Neddleman and Wunsch (1970) (J. Mol. Biol. 48:443), by means of the similarity research method of Pearson and Lipman (1988) (Proc. Natl. Acad. Sci. USA 85:2444), by means of computer softwares using these algorithms (GAP, BESTFIT, FASTA and TFASTA in the Wisconsin Genetics Software Package, Genetics Computer Group, 575 Science Dr., Madison, Wis.). The percentage of identity between two nucleic acid sequences or two proteic sequences is determined by comparing these two aligned sequences in an optimal manner with a "comparison window" in which the region of the nucleic acid sequence or proteic sequence to compare may comprise additions or deletions with regard the sequence of reference for an optimal alignment between these two sequences. The percentage of identity is calculated by determining the number of positions for which the nucleotide or the amino-acid is identical between the two sequences, by dividing this number of identical positions by the total number of positions in the "comparison window" and by multiplying the result obtained by 100, to obtain the percentage of identity between these two sequences.

The step (3) of expanding the antigen-specific Tr1 cell population according to the present invention using feeder cells, offers the following advantages:
The feeder cell expansion system is capable to maintain exponential growth of the antigen-specific Tr1 cell population for at least two or three months in vitro,
The feeder cells lack MHC class I and II molecules to avoid allogeneic response,
The feeder cells are mycoplasma-free,
The feeder cells are capable to grow well using serum free medium,
The feeder cells do not require to be irradiated,
The feeder cells do not allow the expansion of mammal viruses, and
The expanded antigen-specific Tr1 cell population is very well characterized for injection purposes.

The present invention is further described in the following figures and examples. These figures and examples are provided for purposes of illustration only, and are not intended to be limiting the scope of the appended claims. The various scenarios are relevant for many practical situations, and are intended to be merely exemplary to those skilled in the art. Thus, the invention should be construed to encompass any and all variations that become evident as a result of the teaching provided herein.

LEGENDS OF THE FIGURES

FIG. 1: $CD4^+CD18^{bright}CD49b^+$ Tr1 cells proliferate in response to food antigens and not to recall antigens.
A) Purified CD4+ T cells (grey bars), CD4+ CD18brightCD49b+Tr1 cells (white bars) and CD4+ CD45RO+CD49b− memory T cells were stimulated with tetanus toxoid (10 μg/mL), PPD (20 μg/mL) or anti-CD3+ antiCD28 mAb (10 μg/mL) in the presence of autologous purified monocytes. Proliferation was analysed by thymidine incorporation at day 5. B) the same population as in A were stimulated with ovalbumin (OVA, 20 μg/mL), Casein (20 μg/mL) or a mixture of soya proteins (Soya) at 50 μg/mL). Results represent the mean proliferative response of 10 different patients.

Figure 2:
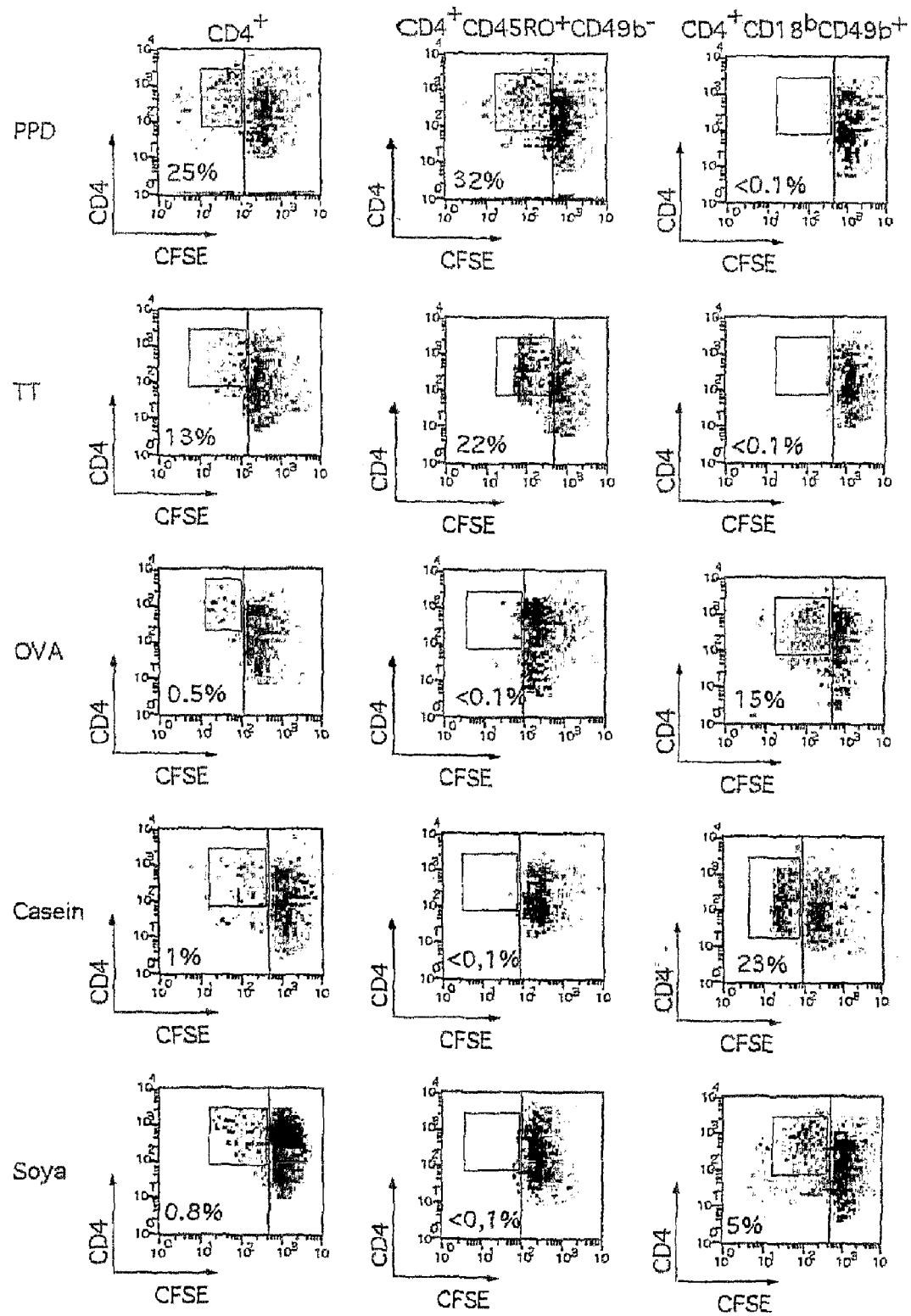

FIG. 2: $CD4^+CD18^{bright}CD49b^+$ T cells proliferate to food antigen and not to vaccine antigen.
$CD4^+$ T cells or purified $CD4^+CD45RO^+CD49b^-$ or $CD4^+CD18^+CD49b^+$ were labelled with CFSE and stimulated with the different antigen as indicated, either vaccine antigen (PPD, purified protein derivative:tuberculin, TT:tetanus toxoid) or food antigen (OVA: ovalbumin, Casein or Soya protein). After 8 days, cells were analyzed by cytofluorometry, and the percentage of divided cells was analyzed by the decreased expression of CFSE. The percentage of $CFSE^{low}$ cells is indicated in each quadrant.

Figure 3:
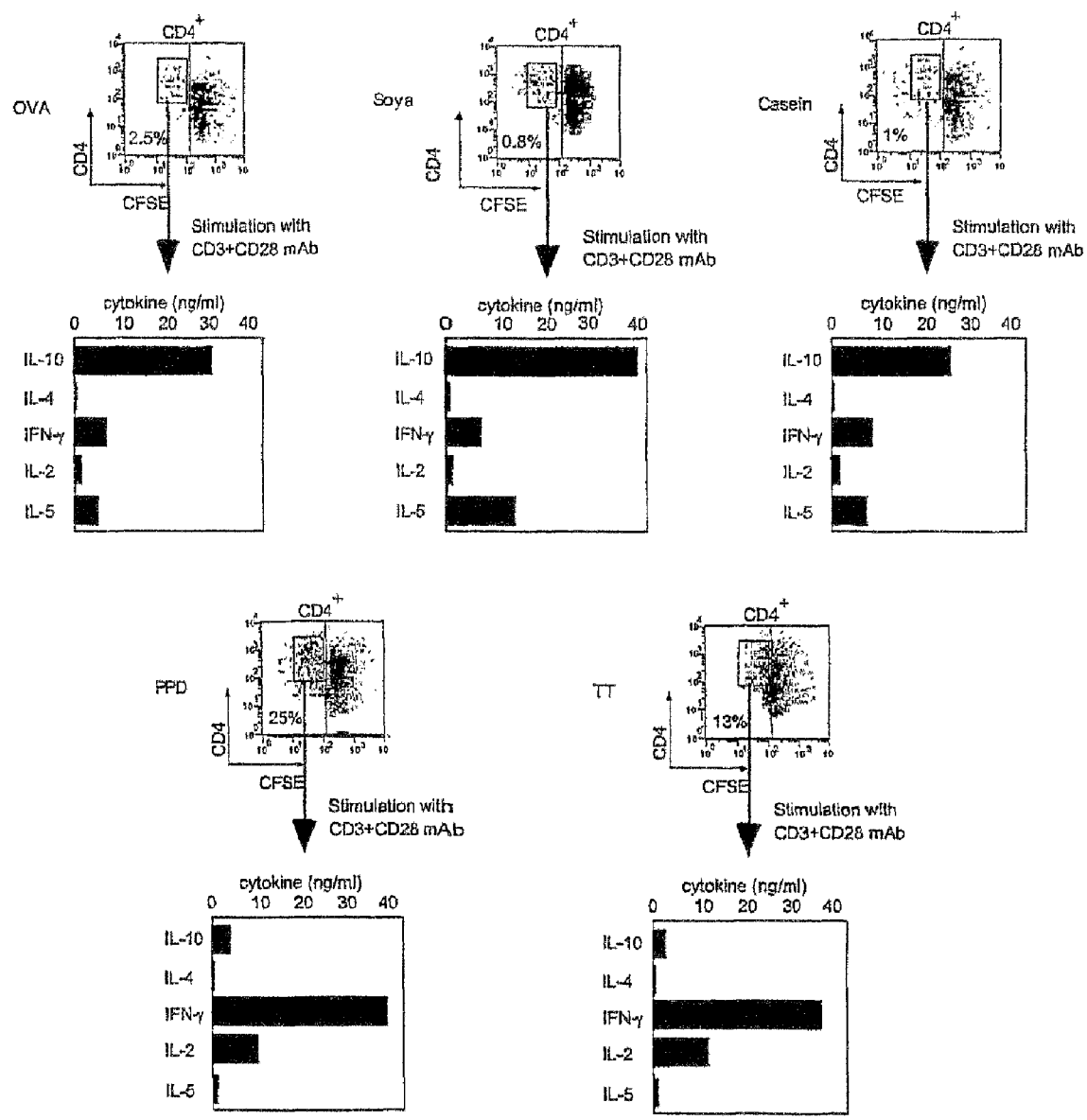

FIG. 3: Food antigen-specific $CD4^+$ proliferative T cells have a Tr1 cytokine profile phenotype.
$CD4^+$ T cells were labelled with CFSE and stimulated with the indicated vaccine (PPD, TT) or food (OVA, Soya, Casein) antigen. $CFSE^{low}$ $CD4^+$ T cells were purified and restimulated with anti-CD3 and anti-CD28 mAb, and after 48 hr the supernatants were analyzed by ELISA to measure the amounts of the indicated cytokines. Food antigen specific proliferative $CD4^+$ T cells displayed a Tr1 phenotype with $IL-10^{high}$ $IL-4^-$ $IFN-g^{+/-}$, $IL-5^{+/-}$, $IL-2^-$ secretion level, whereas recall antigen-specific T cells displayed a Th1 phenotype with high $IFN-\gamma$ secretion.

Figure 4:
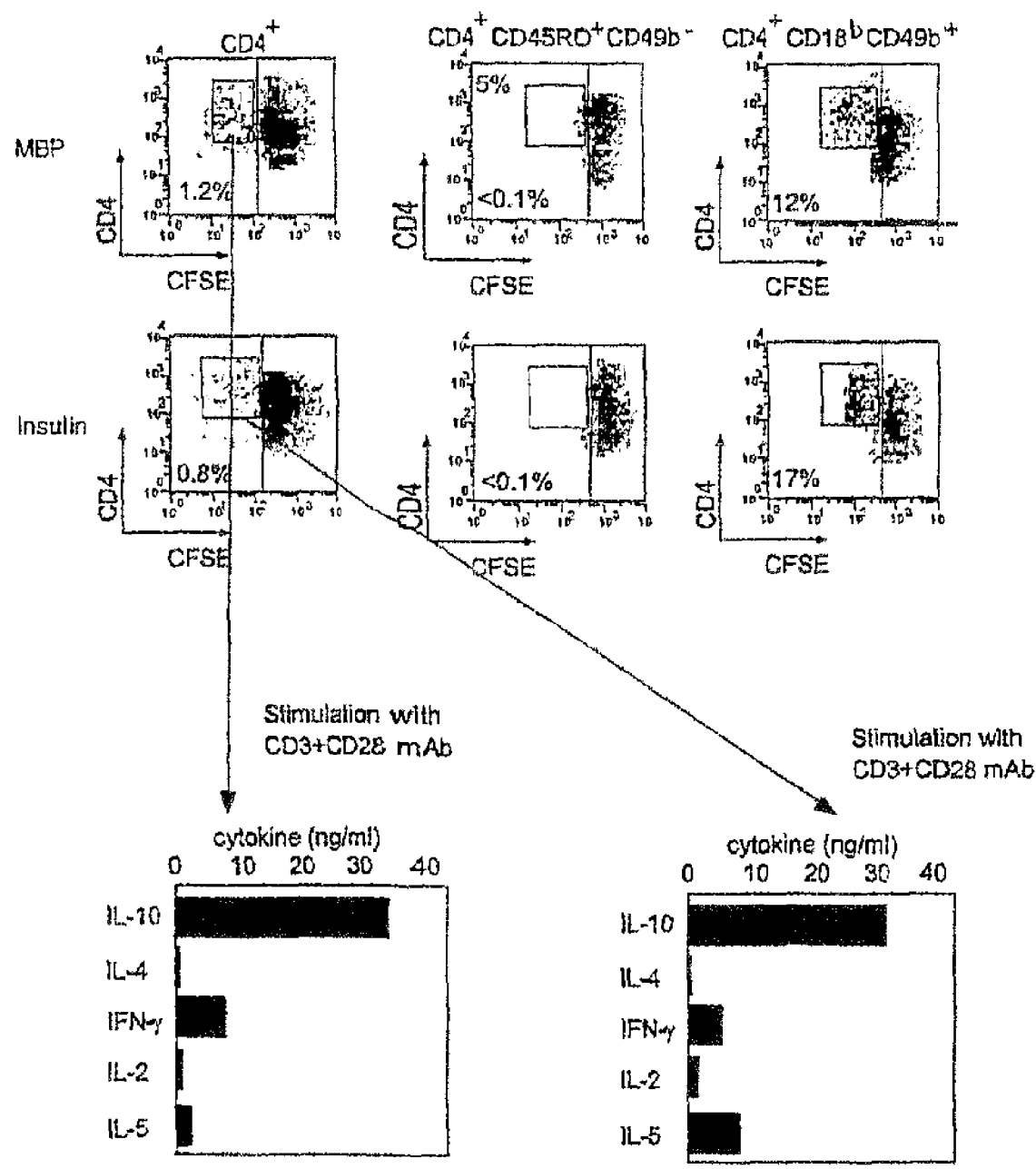

FIG. 4: $CD4^+CD18^{bright}CD49b^+$ T cells proliferate to auto-antigen and auto-antigen-specific cells displayed a Tr1 cytokine phenotype.
$CD4^+$ T cells or purified $CD4^+CD45RO^+CD49b^-$ or $CD4^+CD18^+CD49b^+$ were labelled with CFSE and stimulated with an auto-antigen (MBP: myelin basic protein) or insulin as indicated. After 8 days, cells were analyzed by cytofluorometry, and the percentage of divided cells was analyzed by the decreased expression of CFSE. The percentage of $CFSE^{low}$ cells is indicated in each quadrant. $CFSE^{low}$ T cells were purified and restimulated with anti-CD3 and anti-CD28 mAb, and after 48 hr the supernatants were analyzed by ELISA to measure the amounts of the indicated cytokines. Auto-antigen specific proliferative $CD4^+$ T cells displayed a Tr1 phenotype with $IL-10^{high}$ $IL-4^-$ $IFN-\gamma^{+/-}$, $IL-5^{+/-}$, $IL-2^-$ secretion levels.

Figure 5:
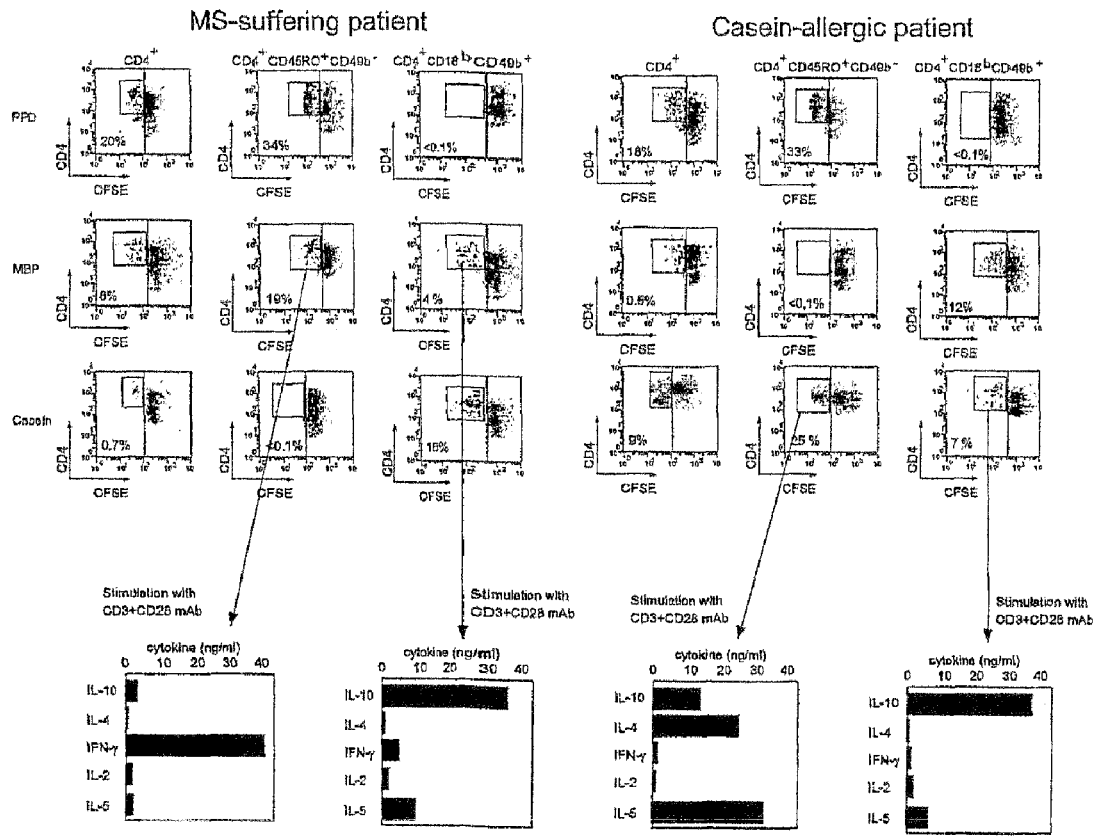

FIG. 5: Tr1 cells can be observed in patients suffering from autoimmune or allergic diseases to the tested antigen
$CD4^+$ T cells or purified $CD4^+CD45RO^+CD49b^-$ or $CD4^+CD18^+CD49b^+$ were isolated from a patient suffering from multiple sclerosis (MS) or allergy to casein as indicated, labelled with CFSE and stimulated with autoantigen (MBP: myelin basic protein), or casein or purified protein derivative from *mycobacterium tuberculosis* (PPD) as a positive control as indicated. After 8 days, cells were analyzed by cytofluorometry, and the percentage of divided cells was analyzed by the decreased expression of CFSE. The percentage of $CFSE^{low}$ cells is indicated in each quadrant. $CFSE^{low}$ T cells were purified and restimulated with anti-CD3 and anti-CD28 mAb, and after 48 hr the supernatants were analyzed by ELISA to measure the amounts of the indicated cytokines.

Figure 6:
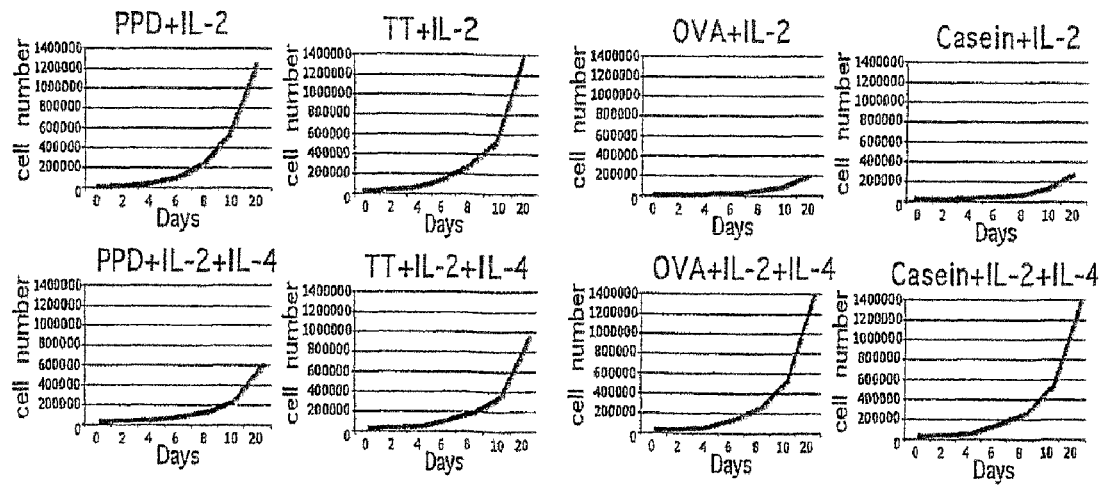

FIG. 6: Food antigen-specific Tr1 Cells did not proliferate in response to IL-2 alone but proliferated vigorously in response to IL-2 and IL-4.
$CD4^+$ T cells were labelled with CFSE, stimulated with the indicated antigens and purified as in FIG. 3. The purified cells were then expanded in the presence of IL-2 alone (1 μg/mL) or IL-2 and IL-4 (1 μg/mL and 500 ng/mL respectively). The number of cells under the different conditions was then measured and plotted against the number of days after initiation. Recall antigen T cells proliferated in response to IL-2 and the combination of IL-2 and IL-4 whereas food-antigen-specific Tr1 cells proliferated only against the combination of IL-2 and IL-4 cytokines.

Figure 7:
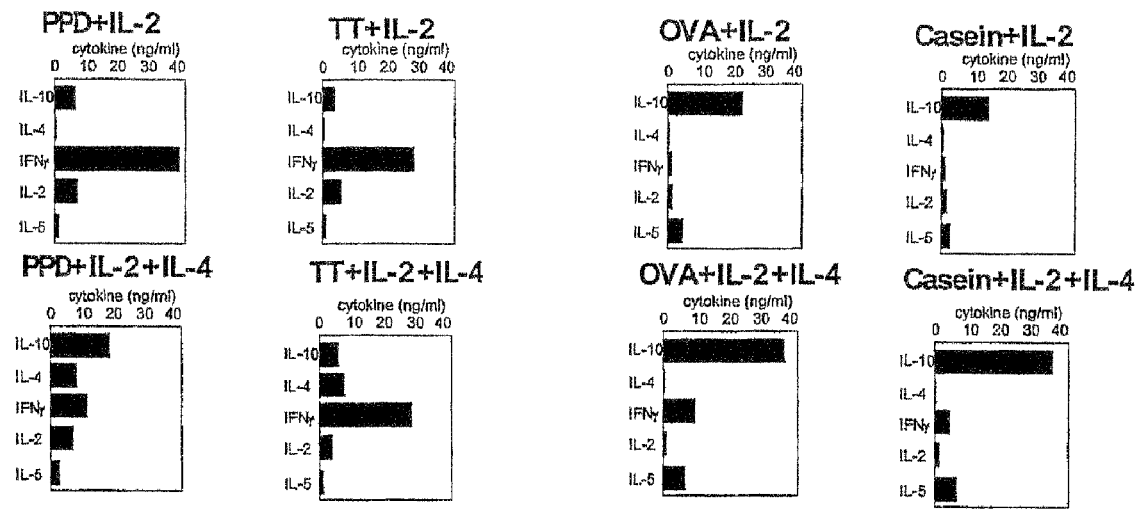

FIG. 7: IL-2 and IL-4 expanded food antigen-specific Tr1 cells maintain their cytokine profile after expansion The different antigen-specific T cell population as obtained in FIG. 5 were stimulated with CD3 and CD28 mAb and their cytokine profile was determined by ELISA in supernatants collected 48 hr after stimulation. PPD- and TT-specific T cells maintained their Th1 cytokine profile after expansion with IL-2 alone, whereas IL-4 addition induced the secretion of IL-4 in these cells as expected. In contrast, food-antigens-specific Tr1 cells maintained their cytokine profile even after expansion in the presence of IL-2 and IL-4.

Figure 8:
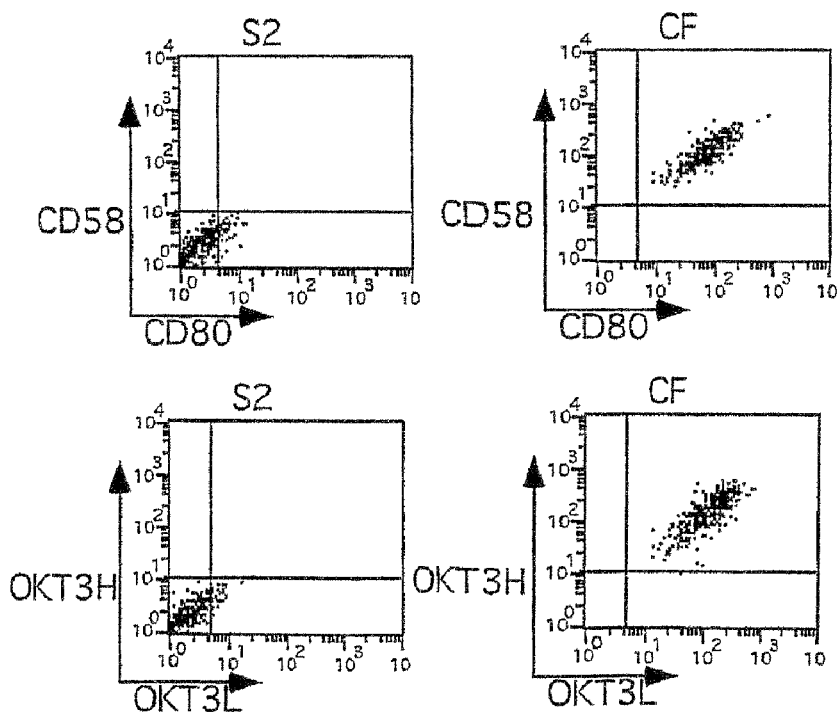

FIG. 8: Analysis of human protein expression on S2 cell line.

Two-color flow-cytometric analysis of OKT3 heavy and light chains and CD80 and CD58 expression in parental (S2) or cell factory (CF) cells.

Figure 9:
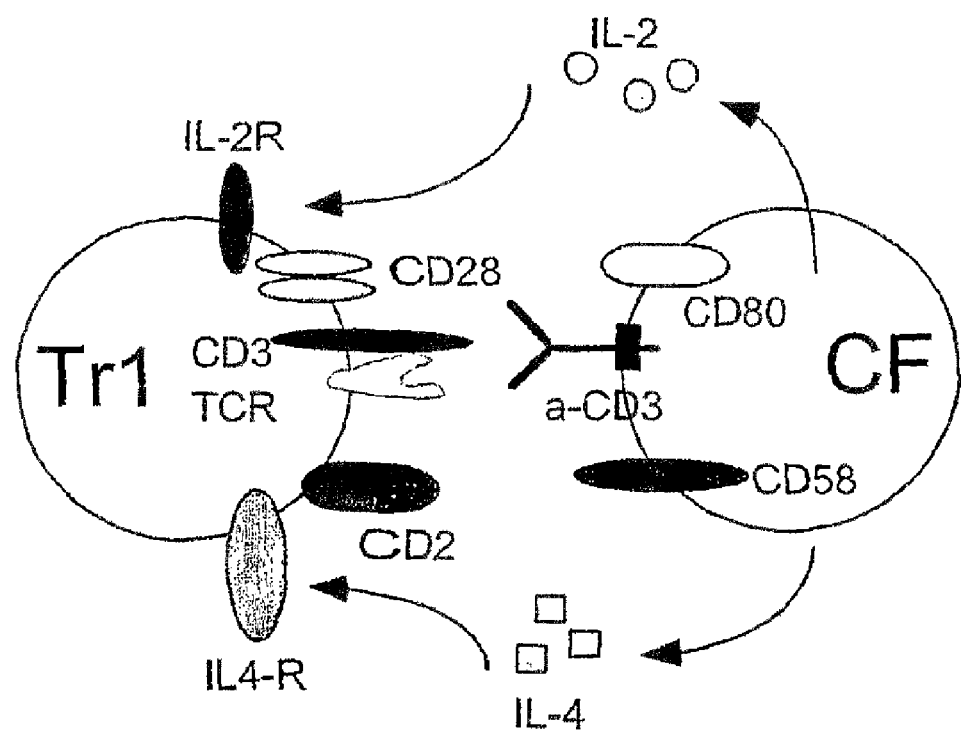

FIG. 9: Cartoon of engineered CF interacting with a CD4+ Tr1 CELL

S2 cells were transfected with a membrane bound anti-CD3 mAb to engage the TCR/CD3 complex, CD80 and CD58 to add some costimulatory signals through interaction with CD28 and CD2 molecules respectively, and IL-2 and IL-4 to enduce cell growth.

Figure 10:
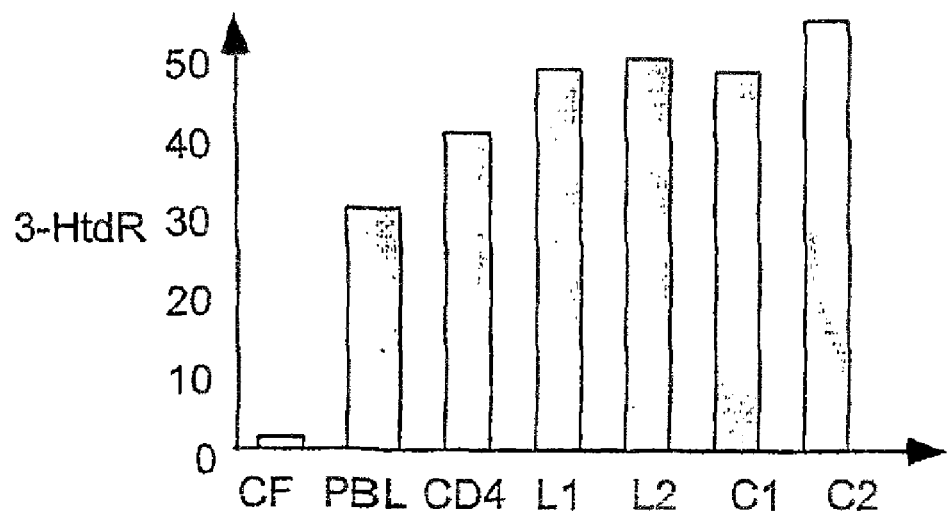

FIG. 10: Proliferation of T cells induced by CF cell line.

Proliferation of polyclonal PBLs, CD4+ T cells Tr1 cells lines (L1 and L2) or Tr1 clones (C1 and C2) stimulated with the cell factory was measured by [3H]thymidine incorporation between days 3 and 4 culture. T cells were stimulated with CF cells as indicated, in the absence of exogenous cytokines. At 72 h, the cells were pulsed with [3H]thymidine and incubated for an additional 18 h before harvesting. Counts per minute values are shown as mean s.e.m. from triplicate cultures.

Figure 11:
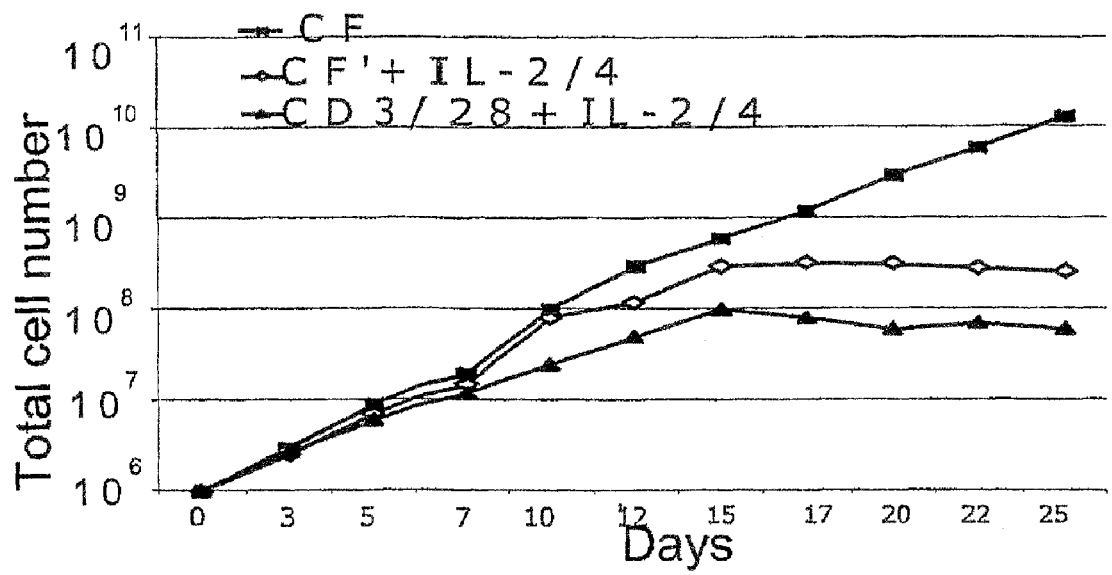

FIG. 11: Long-term growth of primary polyclonal human Tr1 cells stimulated with cell factory.

Tr1 cells were stimulated with CD3/28 beads plus exogeneous IL-2 and IL-4, CF' cells expressing OKT3, CD80 and CD58 but not IL-2 and IL-4 in the presence of exogenous IL-2 and IL-4, or with the complete cell factory system without any exogenous addition. T cells were stimulated with CF cells on days 0, 10, and 20 of culture.

Figure 12:
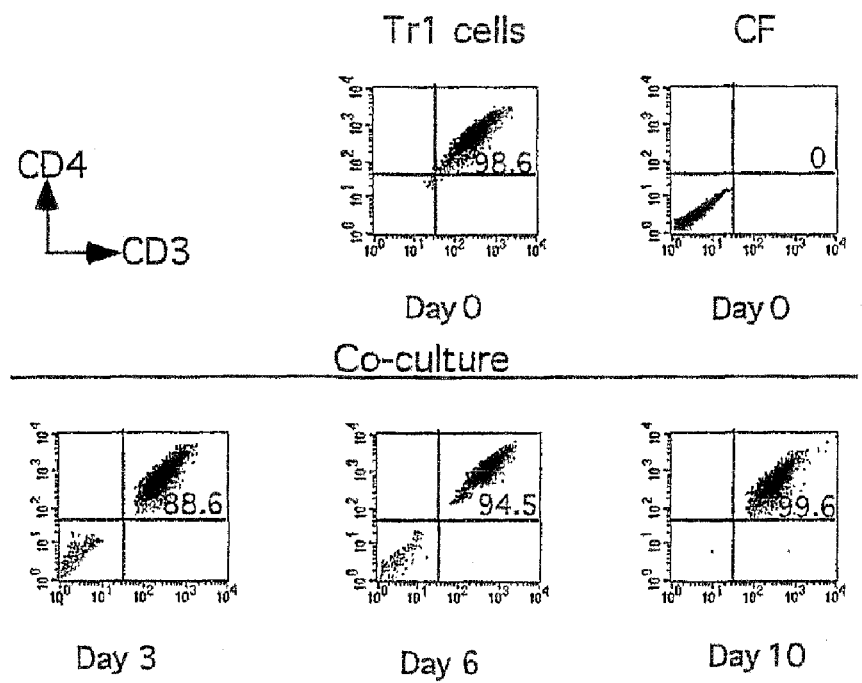

FIG. 12: Purity of T cells after co-culture with CF cell line.

The purity of T cells and after stimulation with CF cell line was assessed by staining for CD3, CD4 expression during the first seven days of culture. Gating on cell size/debris was not used in this experiment so as to represent all cells in the culture. Viable cells are indicated by gating on propidium iodide to exclude dead cells. Results are representative of >10 different experiments, each with a different donor.

Figure 13:
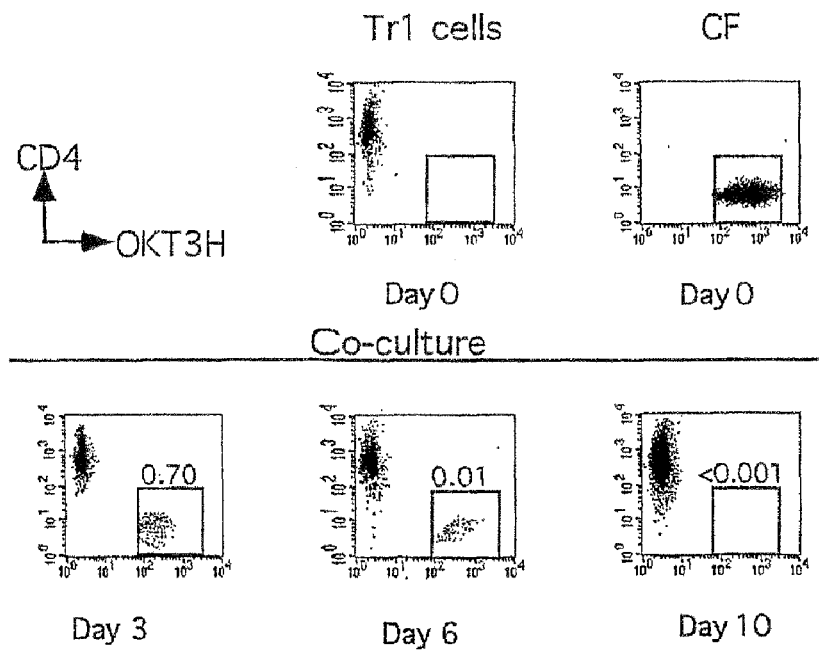

FIG. 13: Fate of CF cell line after co-culture with T cells

The fate of CF stimulator cells were assessed by staining for CD4 and OKT3H expression during the first seven days of culture. Gating on cell size/debris was not used in this experiment so as to represent all cells in the culture. Viable cells are indicated by gating on propidium iodide to exclude dead cells. Results are representative of >10 different experiments, each with a different donor.

Figure 14:
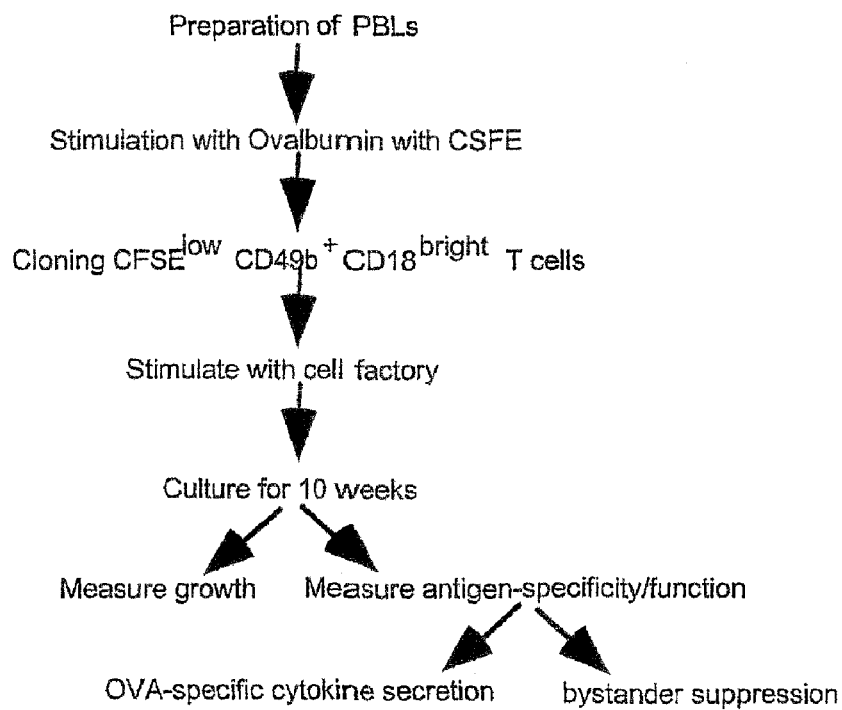

FIG. 14: Schematic representation of the experimental protocol used.

Figure 15:
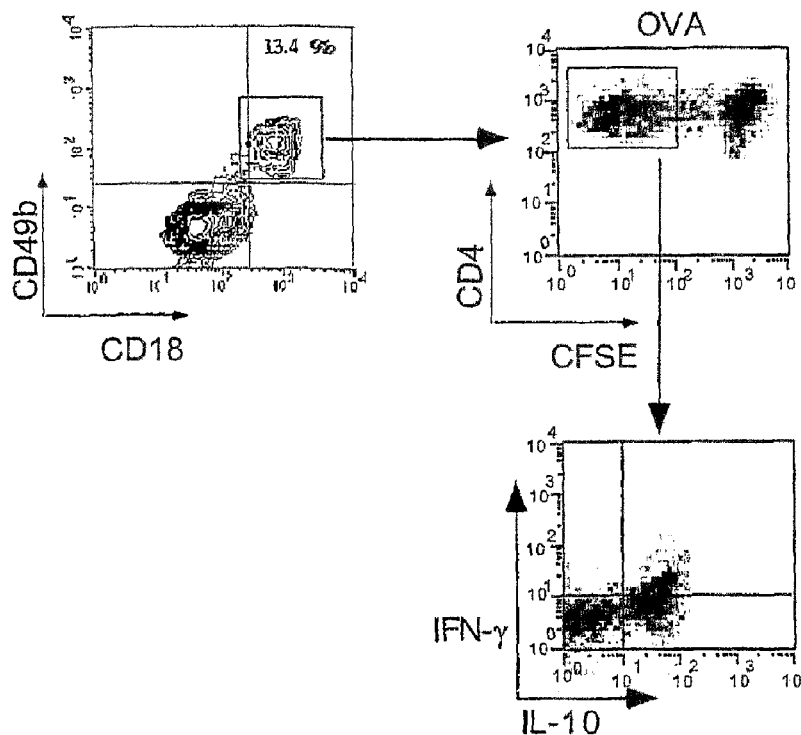

FIG. 15: Isolation of OVA-specific Tr1 clones.

PBL stained with CFSE were stimulated with OVA, and stained with CD4 CD49b and CD18. CD4+CD49b+ CD18$^{bright}$ cells were gated and CFSE cells were sorted. Sorted cells were cloned to generate clone 1 and 2, the bulk population was stimulated with OVA and stained with IL-10 and IFN-γ revealing a Tr1 phenotype.

Figure 16:
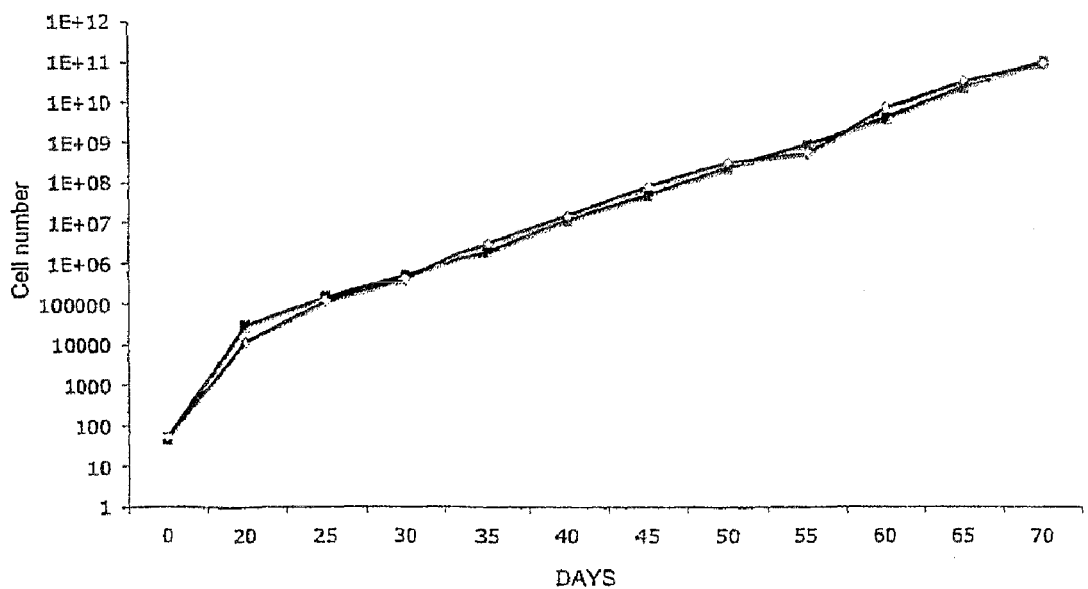

FIG. 16: Analysis of long term proliferation of Tr1 clones

Two clones were then stimulated with the irradiated cell factory. The total cell numbers are depicted in a semi-log plot of cell number vs. days in culture.

Figure 17:
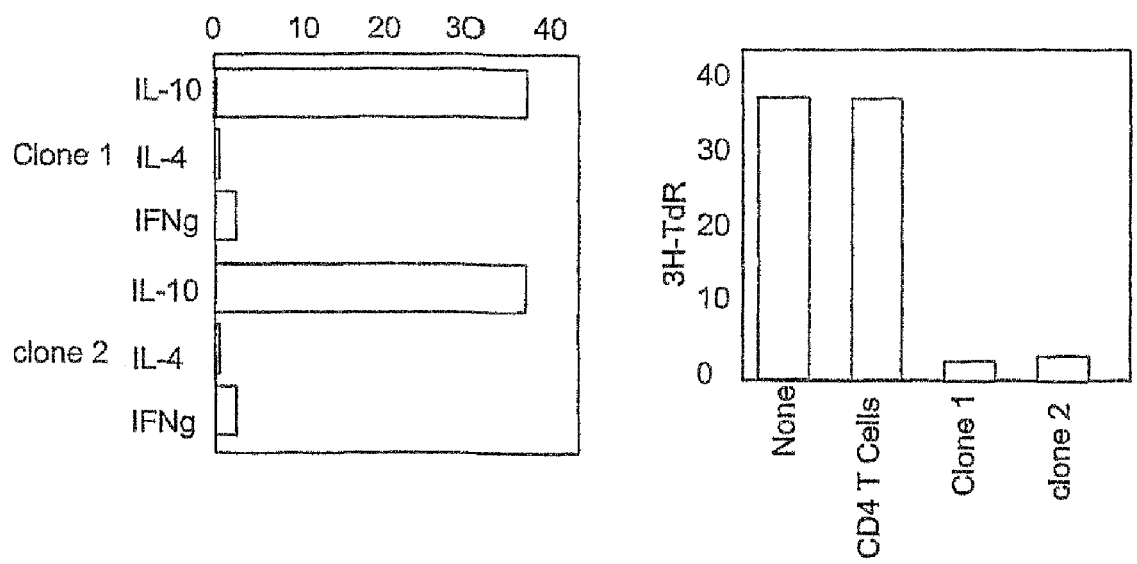

FIG. 17: Cytokine profile of OVA-specific T clones 1 and 2 after expansion on the cell factory for 70 days.

Cytokine were measured in the supernatants of the clones stimulated with OVA and autologous irradiated monocytes. Antigen-specific suppression was also examined by a transwell assay. Autologous PBLs were stimulated with anti-CD3 mAb in the bottom well, no cells, control CD4 T cells and the two clones were added in the top basket and stimulated with anti-CD3 and autologous irradiated monocytes for CD4 cells or OVA and irradiated autologous monocytes for the two Tr1 clones. The entire protocol is representative of ten experiments, each from different donors.

EXAMPLES

Example 1

In Vitro Obtention of a Food- or Auto-Antigen Specific Tr1 Cell Population from a PBMC Population by Stimulation with the Food- or Auto-Antigen 1.1 Material and methods
Cell Purification and Flow Cytometry Human peripheral blood mononuclear cells (PBMC) were recovered from Buffy coats of healthy donors after centrifugation on ficoll gradient. CD4+ T lymphocytes were purified from PBMC after depletion of CD11b+ (OKM1-95), CD20+ (1F5C9), and CD8+ (G42-8) cells by negative selection using Goat anti-mouse-coated Dynabeads (Dynal, Oslo, Norway). Monocytes were purified by adherence after culture of PBMC 1 hour at 37° C. in RPMI supplemented with 20% FCS. More than 90% of the recovered adherent cells were CD14+ monocytes. CD4+ T lymphocytes were separated in CD49b+ CD18$^{bright}$ or CD49b+CD45RO+ T cells after staining the cells with fluorescent antibodies and sorted on a FACS vantage SE, Beckton Dickinson, Le pont de Claix, France). The following antibodies were used for flow cytometry: FITC, APC or PC5-labeled mouse anti-human CD4 (RPA-T4), PC5-labeled mouse anti-human CD3 (UCHT1), PE-labeled mouse anti-human CD49b (12F1-H6), FITC-labeled mouse anti-human CD14 (M5-E2), PE or PC5-labeled mouse anti-human CD18 (6.7), PE-labeled mouse anti-human CD25 (M-A251), PE-labeled mouse anti-human HLA-DR (G46-6), PE-labeled mouse anti-human CD69 (FN50), FITC anti-human CD45RO (UCHL-1). All antibodies were purchased from BD-Pharmingen (Le Pont de Claix, France).

Cell Culture

For detection of CD4+ antigen-specific T lymphocytes, PBMCs (10 millions cells/mL) were stained with either 0.2 μM CFSE or 2.5 μM PKH26 (Molecular Probes, Leiden, Holland) during 5 minutes at 37° C. in PBS 1×. After two washes in PBS 1×, cell populations were incubated at 2 millions/mL in RPMI supplemented with 5% human serum AB in the presence or absence of 200 μg/mL of chicken Ovalbumin, 200 μg/mL of bovine Caseine, 200 μg/mL of human Insulin (Sigma, L'Isle d'Abeau, France), 50 μg/mL of Tetanus toxoid (Lederle, Pearl River, N.Y.) and 2 μg/mL of Purified Protein Derivative (PPD) from *mycobacterium Tuberculosis* (Staten serum Institute, Danmark) or 50 μg/mL of MBP (Sigma, L'Isle d'Abeau, France). After 9 days of culture, cells were stained with PC5-labeled mouse anti-human CD4 and analyzed by flow cytometry. CD49b+CD18$^{bright}$ or CD49b+ CD45RO+ T cells were also sorted, stained with 0.2 μM CFSE or 2.5 μM PKH26 and cultured at 2 millions/mL in the presence of 4·10⁵ autologous monocytes and in the presence of antigens.

Sorting and Expansion of Antigen Specific Cells

After 10 days of culture, CD4⁺CFSE$^{lo}$ or CD4⁺ PKH26$^{lo}$ antigen-specific T cells were sorted on a FACS vantage SE (Beckton Dickinson) and expanded with autologous irradiated PBMCs in the presence of antigens, in X-vivo 15 medium (Biowhittaker, Emerainville, france) supplemented with 10 ng/mL of IL4 and 5 ng/mL of IL2.

Cytokine Detection

Cytokine production was detected by ELISA that were performed on supernatants of human cells populations (2 millions/mL) cultured 48 hours in RPMI supplemented with 10% FCS (Life Technologies, Cergy Pontoise, France) and stimulated with 10 μg/mL of coated anti-CD3 (UCHT1) and 1 μg/mL of soluble anti-CD28 (CD28.2). Antibodies used were anti-IL10 (JES3-9D7), anti-IL4 (8D4), anti-IL2 (17H12), anti-IL5 (39D10) and anti-IFNγ (A35) capture antibodies and NIP-labeled anti-IL10 (JES3-12D8), anti-IL4 (MP4-25D2), anti-IL2 (B33-2), anti-IL5 (5A10) and anti-IFNγ (B27) detection antibodies followed by Peroxydase-labeled anti-NIP antibody and ABTS addition. IL10, IL4 and IFNγ were from R&D systems (Minneapolis, Minn.), IL2 was from Chiron corp (Emmeryville, Calif.). All antibodies were from BD pharmingen.

Proliferation Measurement

To assess proliferation, T cell populations (1 millions cells/mL) were stimulated in vitro with autologous irradiated PBMCs and specific antigens in RPMI supplemented with 10% FCS at 37° C. in the presence of indicated cytokines. T cell proliferation was evaluated by the numeration of live cells.

Methods to Isolate Antigen-Specific Tr1 Cells

The inventors designed methods to isolate populations and clones of antigen-specific Tr1 cells.

The first method relies on CFSE or any similar dye (PHK), incorporation. The cells are labelled with CFSE and stimulation with food antigen (range from 0.1 μg/mL to 5 mg/mL), after 9 to 10 days, the cells are sorted by cytofluorometry and maintained with CD3+CD28 beads and IL-2+IL-4. In order to remove any other cells that could have not significantly proliferated under these culture conditions, the cells could also be cloned at one cell per well and the different clones analysed for specificity and cytokine secretion.

The second method relies on cell surface expression of activation or proliferation markers. The PBMC are stimulated with food or autoantigens and the antigen-stimulated cells are purified by antibodies directed against anti-CD69, anti-CD25 or any activation or proliferation markers. Purified cells are then maintained with CD3+CD28 stimuli and IL-2+IL-4. Alternatively cells can be maintained with feeder cells and CD3/CD28 stimuli, in the presence of IL-2 and IL-4. Purified cells could also be cloned at one cell per well by FACS sorting or limiting dilution.

The third method is based on the enrichment of the proliferative population after stimulation with food or autoantigens. PBMC are stimulated with ovalbumin (or any other food or autoantigen) and after one the week the cells were restimulated with the same antigen in the presence of IL-2 and IL-4. That combination was optimal but any combination or time period could be used. The enriched population was then cloned by limiting dilution (but any other cloning technique could be used). The clones were then multiplied by stimulation with feeder cells anti-CD3, CD28 and IL-2 and IL-4. The proliferating clones were then analysed for specificity and cytokine secretion by using ovalbumin presented by autologous irradiated PBMCs.

1.2 Results

CD4⁺CD3⁺CD49b⁺CD18$^{bright}$ Tr1 Cells Proliferate in Response to Food Antigens and not to Vaccine Antigens.

When the inventors purified CD4⁺CD3⁺CD49b⁺CD18$^{bight}$ Tr1 cells, they observed that these cells did not proliferate in response to recall antigens like tetanus toxoid of PPD, in contrast to the reciprocal population (FIG. 1A). They also tested the ability of CD4⁺CD3⁺CD49b⁺CD18$^{bright}$ Tr1 cells to proliferate to food antigens. As previously reported, only very minimal proliferative response over background was observed when the total CD3⁺CD4⁺ T cell population was stimulated with food antigens (Ovalbumin, casein, soya protein or bovine immunoglobulins). However they observed a vigourous proliferative response in the purified CD4⁺CD3⁺CD49b⁺CD18$^{bright}$ Tr1 cell populations, whereas no proliferation was observed in the reciprocal memory population (FIG. 1B).

They therefore used a more sensitive technique with CFSE incorporation, and observed that Tr1 cells did not proliferate to recall antigens but displayed a significant proliferative response to food antigens like ovalbumin, casein or soya proteins. In contrast the reciprocal population of CD4⁺ T cells did not show any proliferative response to food antigens but proliferated vigorously to recall antigens (TT and PPD) (FIG. 2).

Food Antigen-Specific CD4⁺CD3⁺CD49b⁺CD18$^{bright}$ T Cells have a Tr1 Cytokine Profile.

Using the CFSE incorporation technique (FIG. 3), the inventors isolated by FACS the CFSE$^{low}$ proliferating cells and analyzed their cytokine profile by a polyclonal stimulus (anti-CD3+CD28 mAbs). These experiments showed that OVA, Casein, and soya-specific cells have a Tr1 cytokine profile secreting high levels of IL-10, some IFN-γ, some IL-5 and no IL-2 and IL-4 as previously described (Groux et al. Nature 1997). In contrast, the TT- or PPD-specific cells displayed a Th1 phenotype secreting mainly IFN-γ as expected.

Tr1 Cells are Also Specific for Autoantigens

Using the CFSE technique the inventors also analyzed the proliferative response of the different CD4⁺ T cell populations to autoantigens like MBP (myelin basic protein) or insulin. Similarly to food antigens, minimal to no proliferative response was observed in the bulk CD4⁺ population (as reported) or in the CD49b⁺ memory (CD45RO⁺) population. Surprisingly, vigorous proliferation response was observed when purified CD4⁺CD3⁺CD49b⁺CD18$^{bright}$ Tr1 cells were stimulated with insulin or MBP. Moreover, these insulin- or MBP-specific cells displayed a Tr1 cytokine profile with high IL-10 secretion (FIG. 4).

Tr1 Cells can be Isolated in Patients Suffering from Autoimmunity or Allergy to the Tested Antigen As food antigen and autoantigen have been implicated in allergic or autoimmune diseases respectively, the inventors analyzed the presence of proliferative T cells in the purified CD4⁺CD3⁺CD49b⁺CD18$^{bright}$ T cell population of patients suffering from MS (with an autoimmune disease directed against myelin componant like MBP) or patients with food allergy to casein. As shown in FIG. 5 they observed that, as expected, MBP- or Casein-stimulation induces cell proliferation into the purified CD4⁺CD3⁺CD45RO⁺CD49b⁻ in a patient suffering from multiple sclerosis or Casein-allergy respectively. Restimulation of the proliferative cells showed that as expected these cells displayed a Th1 cytokine profile in the case of the cells from a patient suffering from MS stimulated with MBP, and a Th2 cytokine profile in response to Casein in the case of the allergic patient. However, unexpectedly they also observe a proliferation in the CD4+CD3+CD49b+CD18$^{bright}$ Tr1 cell population as in normal control showing that food or auto-antigen specific Tr1 cells could also be observed in patients suffering of autoimmunity or allergy to the tested antigen (FIG. 5).

The Combination of IL-2 and IL-4 is Required to Maintain the Ag-Specific Tr1 Cell Proliferation.

Although Tr1 cells (CD4+CD3+CD49b+CD18$^{bright}$ cells) proliferated in response to food or autoantigens, that proliferation could not be maintained by the addition of IL-2 alone (FIG. 6) in contrast to the proliferation of TT- or PPD-specific T cells (FIG. 6). Surprisingly, the inventors found that the combined addition of IL-2 and IL-4 was able to maintain the proliferative response of food antigens or autoantigen specific Tr1 cells (FIG. 7).

Example 2

Expansion of the Obtained Antigen-Specific Tr1 Cell Population Using Feeder Cells 2.1 Experimental Protocol
Labelled Antibodies
For Bead Sorting:
  Beads used:
  << MagCellect Ferrofluid, Streptavidin>> (R&D)
  << Sheep anti-Rat beads>> (Dako)
  For CD80: biotinylated mouse-anti-human CD80 (B7-1), clone L307.4 (BD Biosciences Pharmingen)
  For OKT3: purified Rat-anti-mouse Ig Kappa light chain, clone 187.1 (BD Biosciences Pharmingen)
For FACS Sorting and Usual Control Markers
  For CD80: mouse-anti-human CD80-PE (phycoerythrine) or FITC (fluorescein isothiocyanate), clone L307.4 (BD Biosciences Pharmingen)
  For CD58: mouse-anti-human CD58-PE or PECy5 (phycoerythrin-cyanin 5) (LFA-3) Clone 1C3 (BD Biosciences Pharmingen)
  For OKT3:
    Heavy chain: biotinylated anti-mouse IgG2a, clone R19-15+Streptavidine-FITC or Streptavidine-PE or Streptavidine-PECy5 (BD Biosciences Pharmingen)
    Light chain: purified Rat-anti-mouse Ig Kappa light chain, clone 187.1 (BD Biosciences Pharmingen)+Rabbit-anti-Rat-FITC (Dako)

```
Amplifications primers
OKT3-L FWD:
                                      (SEQ ID NO 9)
5'- ATGCGGATCC ATGGATTTTCAAGTGCAG - 3'

OKT3-L REV:
                                     (SEQ ID NO 10)
5'- ATGCGAATTCCTAACACTCATTCCTGTTG - 3' primer OKT3H1 variable heavy chain (571 pb):
HSPAT1 FWD:
                                     (SEQ ID NO 11)
5'- ATG CCC GCG GGG TAC CCA CTG AAA ACT CTG ACT

CAA C - 3'

OKT3 H2/3 REV:
                                     (SEQ ID NO 12)
5'- ACT GGA CAG GGA TCC AGA GTT C - 3' primer OKT3H2 heavy chain CH1-CH3 (850 pb).
OKT3 H3/5 FWD:
                                     (SEQ ID NO 13)
5'- GAA CTC TGG ATC CCT GTC CAG TG - 3'

OKT3 H3/3 REV:
                                     (SEQ ID NO 14)
5'- ATG CGA ATT CTT TAC CCG GAG TCC GGG AGA AGC

TC - 3' primer pdgf platelet-derived growth factor
receptor, beta (151 pb)
PDGFR 5 FWD:
                                     (SEQ ID NO 15)
5'- ATG CGA ATT CGC TGT GGG CCA GGA CAC GCA G -3'

PDGFR 3 REV:
                                     (SEQ ID NO 16)
5'- ATG CGG GCC AAA GCT TCT AAC GTG GCT TCT TCT

GCC AAA G- 3'

IL-2 FWD:
                                     (SEQ ID NO 17)
5' - ATGCGGATCCATGTACAGGATGCAACTCCT - 3'

IL-2 REV:
                                     (SEQ ID NO 18)
5'- ATGCGAATTCTCAAGTCAGTGTTGAGATGA - 3'

LFA3 FWD:
                                     (SEQ ID NO 19)
5'- ATGCTGGATCCATGGTTGCTGGGAGCGACGC- 3'

LFA3 REV:
                                     (SEQ ID NO 20)
5'- ATGCTAAGCTTTCAATTGGAGTTGGTTCTGT- 3'

IL-4 FWD:
                                     (SEQ ID NO 21)
5'- ATGCGGATCCATGGGTCTCACCTCCCAACT- 3'

IL-4 REV:
                                     (SEQ ID NO 22)
5'- ATGCAAGCTTTCAGCTCGAACACTTTGAAT- 3'
```

Cloning and Construction of Cell Factory

Human CD80, IL-2, IL-4 and CD58 were cloned from peripheral blood T lymphocytes (PBLs) obtained from a healthy donor into the pAC vector (Invitrogen) using an insect actin promotor (Chung and Keller, Mol Cell Biol. 1990 December; 10(12):6172-80; Chung and Keller, Mol Cell Biol. 1990 January; 10(1):206-16) and transfected by electroporation (electroporator Biorad, US) into S2 cells from the S2 cell line deposited on Mar. 25, 2005 at the CNCM under the number I-3407. Similarly, the heavy and light chains of OKT3 (Kung et al, *Science*. 1979 Oct. 19; 206(4416):347) were cloned from the OKT3 hybridoma cells (ATCC CRL 8001; Manassas, Va., USA) into the pAC vector and transfected into S2 cells before FACS. To obtain membrane bound anti-CD3 mAb the 3' end of the heavy chain was removed and replaced by the transmembrane part of the platelet derived growth factor (PDGF) gene CF' cells, that is to say cells expressing hCD80, hCD58 and anti-CD3 monoclonal antibody (mAb) and CF, that is to say cells expressing hCD80, hCD58, hIL-2 hIL-4 and anti-CD3 monoclonal antibody (mAb) were isolated by fluorescence-activated cell sorting FACS using the antibodies as described above. No selection marker was used and the stably transfected cells were selected by FACS staining. The sorted cells were cloned and for each round of transfection and selection, the most efficient clone for the stimulation of Tr1 cells was selected.

CD4+ T-Lymphocyte Preparation and S2 Cell Culture

Fresh peripheral blood lymphocytes were obtained by Ficoll hypaque centrifugation, and CD4+ T cells were purified by negative selection using anti-CD8 antibody (Becton Dickinson). All cultures were maintained in X-vivo without serum addition (BioWhittaker, Walkersville, Md.). Human IL-2 (Chiron Therapeutics, Emeryville, Calif.) was added at 20 IU/mL where indicated, hIL-4 was used at 1 μg/mL (for comparing the biological advantage obtained when feeder cells express the interleukins with the results obtained when recombinant intereukins are added in the culture medium). S2 cells were maintained in SFM medium without serum (Gibco).

Flow Cytometry and FACS Sorting

Cells were stained with antibodies at 4° C., and analyzed on a FACSCalibur (BD BioSciences, Mountain View, Calif.) or sorted with the FACStar system.

2.2 Results

Construction of aAPCs

To test the hypothesis that Tr1 cells have distinct co-stimulation requirements for long-term growth, the inventors designed a cell-based system that could be genetically manipulated to express different co-stimulatory molecules and cytokines in addition to CD3/CD28 classical stimuli. They chose S2 cells because they do not express human HLA proteins that would promote allogeneic responses, and they could not be contaminated by human viruses (FIG. 8). Also, the eventual introduction of irradiated feeder cells into the clinical setting can be avoided because these cells which grow at 27° C. are easily killed at 37° C. and are propagated in serum-free medium. The inventors transfected and then cloned S2 cells expressing the human CD80, the human CD58 and the two chains of an anti-hCD3 mAb to permit the stimulation of human Tr1 cells (CF') (FIG. 8). Similarly, they generated the CF line (FIGS. 8, 9) by transfecting CF' cells with human IL-4 and IL-2 cDNA. Cultures were initiated by adding CF cells to fresh human CD4+ T cells prepared by negative selection (see Experimental Protocol).

CF Cell Line Efficiently Activate Human Polyclonal CD4+ T Cells and Tr1 Cells

The cell factory was tested for its ability to stimulate the initial activation and proliferation of primary CD4+ T cells as well as Tr1 cell lines or Tr1 cell clones. The different purified T cells were stimulated with the cell factory at an 1/1 ratio. The inventors found that the initial rate of growth of the T cells stimulated with the cell factory was equivalent, as judged by [3H]thymidine incorporation (FIG. 10) with a slight enhancement of Tr1 cells proliferative response over other CD4+ T cells. The inventors confirmed this observation by labeling fresh T cells with carboxyfluorescein diacetate succinimidyl ester (CFSE) and tracking cell division during the first five days of culture (data not shown). They also found that the cell-based system was more efficient than CD3/28 beads for the induction of proliferation and cell division of CD4+ T cells (data not shown). No proliferation was seen when the cell factory, or CD4+ T cells incubated separately (FIG. 10 and data not shown). Thus, the requirements for the initial rounds of CD4+ T-cell proliferation was even more satisfactory with the cell factory as compared to CD3/CD28 stimulation provided in the context of polystyrene beads.

CF Cell Line Permit Long-Term Expansion of Human Tr1 Cells

Next, the inventors determined whether the cell factory was sufficient to maintain long-term propagation of Tr1 cells (FIG. 11). Tr1 cells were stimulated with CF that secrete hIL-2 and IL-4, with CF' that do not secrete cytokine but with addition of exogenous cytokines and, CD3/28 beads with exogenous cytokines. CD3/28 bead-stimulated cells failed to proliferate after the second stimulation, in agreement with previous studies. Similarly, Tr1 cells stimulated with CF' in the context of IL-2 and IL-4 added exogeneously entered into a plateau phase of the growth curve within two to three weeks of culture, and no additional net growth of cells occurred after re-stimulation. In contrast, when Tr1 cell cultures were stimulated with the cell factory, they remained in exponential growth even after a third stimulation. This augmentation of long-term proliferation was reproducible, as the average increase in the total number of T cells was 810-fold higher in cultures stimulated with the cell factory than in cultures stimulated with CD3/28 beads in six independent experiments.

Phenotypic analysis of cultures showed a progressive enrichment for CD3+CD4+ T cells after stimulation with the cell factory (FIG. 12). The S2 cells rapidly disappeared from the cell culture, as evidenced by an inability to detect the cells expressing the anti-CD3 mAb by flow cytometry after seven days (FIG. 13); this finding was confirmed in large-scale experiments and also by RT-PCR for drosophila genes (data not shown). Thus, the mixed T-cell and cell factory culture yields a population of pure T cells within one week.

Efficient Propagation of Antigen-Specific Tr1 Cells by the Cell Factory

Immunotherapy with Tr1 cells will likely require cells with antigen-specific regulatory functions. To determine whether the cell factory could be used to expand antigen-specific Tr1, the inventors used them to culture OVA-specific Tr1 clones for 10 weeks (FIG. 14). An example of two different clones is shown by the experiment has been performed with hundreds of different antoantigens- or food antigen-specific T cell clones. PBLs from a normal individual were labeled with CFSE to follow cell division and the cells were stimulated with ovalbumin (20 μg/mL) for 7 days. Cells were then stained with CD4, CD18 and CD49b to select for Tr1 cells overexpressing these markers and OVA-specific cells were sorted according to the decrease in CFSE labelling due to antigen-specific cell division (FIG. 15). To control their phenotype a bulk sorted population was stimulated with OVA and cytokine production was analyzed by intracytoplasmic staining which revealed a typical Tr1 population (FIG. 15). After cloning, the cells were stimulated with the cell factory (FIG. 16). All cells were re-stimulated with the cell factory at 10-days intervals. No specific OVA stimulation was provided during culture. Exponential growth curves of both clones were obtained for several months. The one antigen-specific Tr1 cell yielded $1.5 \, 10^9$ cells after one and an half month of culture, a number of cells sufficient for immunotherapy. The substantial proliferative capacity of the Tr1 cells that remains after 30 days of culture suggests that these Tr1 could have substantial long-term engraftment potential after adoptive transfer.

To determine if antigen specificity of the expanded populations was maintained during culture, cells were stimulated with OVA (FIG. 17). After one month and an half of culture, the cells were stimulated with OVA and autologous APCs and cytokine secretion was analyzed. A typical Tr1 profile was observed for the two different clones analyzed.

To examine the effector function of the cultured Tr1 cells, the antigen-specific suppressive function was tested in a typical transwell assay (FIG. 17 and data not shown). Both clones displayed a typical Tr1 suppressive effect on bystander cells. Suppression was due to IL-10 and TGF-β secretion as shown by the use of blocking antibodies (not shown). No suppression was obtained in the absence of OVA stimulation (data not shown). Similar results were obtained with different donors and different Tr1 clones (data not shown).

The invention claimed is:

1. An in vitro method for the obtention of a food- or auto-antigen specific human Tr1 cell population from a human leukocyte population or a human peripheral blood mononuclear cell (PBMC) population, said method comprising:
   1) stimulating the human PBMC or human leukocyte population with the human food- or auto-antigen to obtain a human food- or auto-antigen stimulated cell population, wherein the human food- or auto-antigen is in a soluble form; and
   2) recovering the food- or auto-antigen specific human Tr1 cell population from the human food- or auto-antigen stimulated cell population.

2. The method of claim 1, wherein the food- or auto-antigen specific human Tr1 cell population is obtained from a human PBMC population.

3. The method of claim 2, wherein the human PBMC population stimulated at step (1) contains from $0.01 \times 10^6$ to $100 \times 10^6$ cells/mL.

4. The method of claim 3, wherein the food- or auto-antigen used for stimulation of the PBMC population at step (1) is in a soluble form from 0.1 µg/mL to 5 mg/mL.

5. The method of claim 1, wherein the human PBMC or human leukocyte population is re-stimulated at least once with the same antigen after step (1), in the presence of interleukin-2 (IL-2) and at least one interleukin selected from the group consisting of interleukin-4 (IL-4) and interleukin-13 (IL-13).

6. The method of claim 1, wherein the food- or auto-antigen is an antigen obtained by synthesis or by recombinant techniques.

7. The method of claim 1, wherein the food-antigen is selected from the group consisting of ovalbumin, casein, soya protein and mixtures thereof.

8. The method of claim 7, wherein the food-antigen is selected from the group consisting of chicken egg ovalbumin of sequence SEQ ID NO 23, bovin alpha S1-casein of sequence SEQ ID NO 24, bovin beta-casein of sequence SEQ ID NO 25, and sequences having at least 70% of identity with one of the sequences SEQ ID NO 23, SEQ ID NO 24 and SEQ ID NO 25.

9. The method of claim 1, wherein the auto-antigen is selected from the group consisting of insulin, myelin basic protein and mixtures thereof.

10. The method of claim 1, wherein the human PBMC or human leukocyte population is incubated, before stimulation at step (1), with a cell division fluorescent marker allowing to determine, by cytofluorometry, that when the fluorescence intensity of the stimulated cell population is at least twice lower than the fluorescence intensity of the human PBMC or human leukocyte population, that cell division has occurred in said stimulated cell population, and that said stimulated cell population which is recovered at step (2) comprises the antigen-specific human Tr1 cell population.

11. The method of claim 10, wherein the cell division fluorescent marker is the carboxyfluorescein diacetate succinimidyl ester (CFSE) marker, the oregon green 488 carboxylic acid diacetate (Carboxy-DFFDA SE) marker or the PKH26 marker.

12. The method of claim 1, wherein the antigen-specific human Tr1 cell population is recovered at step (2) by cytofluorometry using fluorescent labelled antibodies directed against proteins present at the surface of the cells of said antigen-specific Tr1 cell population.

13. The method of claim 1, wherein the antigen-specific human Tr1 cell population is recovered at step (2) by a cloning technique.

14. The method of claim 1, which further comprises:
   3) expanding the antigen-specific human Tr1 cell population recovered at step (2) in a culture medium Mp adapted to Tr1 cells.

15. The method of claim 14, wherein the step (3) of expanding the antigen-specific human Tr1 cell population consists in contacting said cell population with CD3+CD28 beads in the presence of IL-2 and IL-4.

16. The method of claim 14, wherein the step (3) of expanding the antigen-specific human Tr1 cell population requires the presence of a group of factors in the culture medium Mp adapted to Tr1 cells, said expanding step comprising:
   a) cultivating feeder cells capable of expressing the factors of said group at a temperature $T_1$ in a culture medium Mf adapted to feeder cells, such $T_1$ allowing the proliferation of said feeder cells,
   b) contacting the feeder cells obtained at step (a) cleared or not of their culture medium Mf, with the antigen-specific human Tr1 cell population contained in the culture medium Mp, wherein said culture medium Mp does not initially contain the group of factors, in order to obtain a mixture containing the antigen-specific human Tr1 cell population, feeder cells and the culture medium Mp, c) cultivating the mixture obtained at step (b) containing the factors of the group which are expressed by the feeder cells in the culture medium Mp, wherein said step (c) of cultivating is carried out at a temperature $T_2$ which is at least 34.9° C., such that:

the antigen-specific human Tr1 cell population proliferates, and the feeder cells do not proliferate, and wherein the antigen-specific human Tr1 cell population is expanded, d) recovering the antigen-specific human Tr1 cell population so expanded.

17. The method of claim 16, wherein the feeder cells die during step (c).

18. The method of claim 17, wherein at step (d) the cell membrane fragments of the feeder cells that result from death of said cells are eliminated.

19. The method of claim 16, wherein the group of factors comprises factors anchored to the cell membrane of the feeder cells and factors secreted by said feeder cells.

20. The method of claim 16, wherein the factors of said group bind to cell surface proteins of the antigen-specific human Tr1 cell population to be expanded.

21. The method of claim 16, wherein the feeder cells do not naturally express class I and/or II major histocompatibility complex (MHC) molecule at their surface.

22. The method of claim 16, wherein at step (b) the feeder cells are cleared of their culture medium Mf.

23. The method of claim 16, wherein the feeder cells are insect feeder cells, with $T_1$ being lower than $T_2$.

24. The method of claim 23, wherein the insect feeder cells are from the S2 *Drosophilia* cell line.

25. The method of claim 16, wherein the culture medium Mp is a serum-free culture medium.

26. The method of claim 16, wherein the culture medium Mf is a serum-free culture medium.

27. The method of claim 16, wherein the feeder cells are recombinant cells and contain heterologous nucleic acids encoding the factors of said group.

28. The method of claim 27, wherein the feeder cells are recombinant feeder cells expressing the group of factors which bind to the following cell surface proteins of the antigen-specific human Tr1 cell population to be expanded:

the CD3/TCR protein complex,
the CD28 protein,
the CD2 protein,—the interleukin-2 (IL-2) receptor, and
the interleukin-4 (IL-4) receptor.

29. The method of claim 28, wherein the group of factors comprise:

the modified anti-CD3 antibody, wherein the modification of the anti-CD3 antibody consists in the replacement of the anti-CD3 intracytoplasmic domain of the anti-CD3 heavy chain with a transmembrane domain, said modified anti-CD3 antibody being anchored to the cell membrane of the feeder cells the CD80 or CD86 protein, preferably the CD80 protein, anchored to the cell membrane of the feeder cells, and the CD58 protein anchored to the cell membrane of the feeder cells, the IL-2 secreted by the feeder cells, and an interleukin selected from the group comprising IL-4 and interleukin 13 (IL-13), said interleukin being secreted by the feeder cells.

30. The method of claim 29, wherein the transmembrane domain which replaces the intracytoplasmic domain of the anti-CD3 antibody heavy chain is the transmembrane domain of the platelet derived growth factor (PDGF).

31. The method of claim 30, wherein the factors of said group are of human origin.

32. The method of claim 31, wherein the light chain of the modified anti-CD3 antibody is encoded by the heterologous nucleic acid of sequence SEQ ID NO 1 or any nucleic acid having at least 70% of identity with SEQ ID NO 1, and wherein the heavy chain of the modified anti-CD3 antibody is encoded by the heterologous nucleic acid of sequence SEQ ID NO 2, or any nucleic acid having at least 70% of identity with SEQ ID NO 2.

33. The method of claim 31, wherein the CD80 protein is encoded by the heterologous nucleic acid of sequence SEQ ID NO 3, or any nucleic acid having at least 70% of identity with SEQ ID NO 3.

34. The method of claim 31, wherein the CD 86 protein is encoded by the heterologous nucleic acid of sequence SEQ ID NO 4, or any nucleic acid having at least 70% of identity with SEQ ID NO 4.

35. The method of claim 31, wherein the CD58 protein is encoded by the heterologous nucleic acid of sequence SEQ ID NO 6, or any nucleic acid having at least 70% of identity with SEQ ID NO 6.

36. The method of claim 31, wherein the IL-2 is encoded by the heterologous nucleic acid of sequence SEQ ID NO 5, or any nucleic acid having at least 70% of identity with SEQ ID NO 5.

37. The method of claim 31, wherein the IL-4 is encoded by the heterologous nucleic acid of sequence SEQ ID NO 7 or any nucleic acid having at least 70% of identity with SEQ ID NO 7.

38. The method of claim 31, wherein the IL-13 is encoded by the heterologous nucleic acid of sequence SEQ ID NO 8, or any nucleic acid having at least 70% of identity with SEQ ID NO 8.

39. The method of claim 31, wherein the antigen-specific human Tr1 cell population so expanded is recovered at step (d) after having cultivated the antigen-specific human Tr1 cell population at step (c) during at least 12 hours.

* * * * *